United States Patent
Kimchy et al.

(10) Patent No.: US 9,392,961 B2
(45) Date of Patent: *Jul. 19, 2016

(54) INTRA-LUMEN POLYP DETECTION

(75) Inventors: Yoav Kimchy, Haifa (IL); Yitzak Klein, Kiryat Yam (IL); Gideon Baum, Haifa (IL); Rafi Sommer, Nesher (IL)

(73) Assignee: CHECK-CAP LTD., Isfyia (IL)

(*) Notice: Subject to any disclaimer, the term of this patent is extended or adjusted under 35 U.S.C. 154(b) by 335 days.

This patent is subject to a terminal disclaimer.

(21) Appl. No.: 12/825,797

(22) Filed: Jun. 29, 2010

(65) Prior Publication Data

US 2010/0303200 A1 Dec. 2, 2010

Related U.S. Application Data

(63) Continuation-in-part of application No. 10/596,065, filed as application No. PCT/IL2004/001140 on Dec. 16, 2004, now Pat. No. 7,787,926, which is a continuation-in-part of application No. 12/525,672, (Continued)

(51) Int. Cl.
*A61B 5/05* (2006.01)
*A61B 5/07* (2006.01)
(Continued)

(52) U.S. Cl.
CPC ............... *A61B 5/073* (2013.01); *A61B 5/036* (2013.01); *A61B 5/42* (2013.01); *A61B 6/4057* (2013.01); *A61B 6/425* (2013.01); *A61B 6/4258* (2013.01); *A61B 6/482* (2013.01); *A61B 6/4241* (2013.01)

(58) Field of Classification Search
CPC .. A61B 19/5244; A61B 5/055; G01N 23/223; G21K 1/06

USPC .......................................................... 378/44
See application file for complete search history.

(56) References Cited

U.S. PATENT DOCUMENTS 4,217,045 A    8/1980  Ziskind
4,653,081 A *  3/1987  Sipila et al. ............ 378/45
(Continued)

FOREIGN PATENT DOCUMENTS

EP      0390478       10/1990
JP      2003-038424   2/2003
(Continued)

OTHER PUBLICATIONS

Caner B.E., et al., "Functional assessment of human gastrointestinal tract using 99Tcm-latex particles", Abstracat Only, Nucl. Med. Commun., 12(6):539-544 (1991).
(Continued)

*Primary Examiner* — Tse Chen
*Assistant Examiner* — Hien Nguyen
(74) *Attorney, Agent, or Firm* — Soroker Agmon Nordman

(57) ABSTRACT

An apparatus and a method for detecting clinically-relevant features of the gastrointestinal (GI) tract of a subject are disclosed. The apparatus includes a capsule to be swallowed by a subject and passing through the GI tract of the subject, a capsule housing, a radiation source emitting radiation, a rotatable collimator configured to rotate with respect to the housing and to collimate the radiation emitted by the radiation source, and a radiation detector configured to detect particles, such as photons, gamma radiation, beta radiation and electrons photons generated responsive to the emitted radiation. The apparatus also includes a control unit configured to analyze data regarding the photons. Movement of the capsule in the GI tract can be detected. The radiation source, radiation detector and control unit may advantageously be integrated inside a single housing.

21 Claims, 18 Drawing Sheets

Related U.S. Application Data filed as application No. PCT/IL2008/000163 on Feb. 6, 2008.

(60) Provisional application No. 60/531,690, filed on Dec. 17, 2003, provisional application No. 60/559,695, filed on Mar. 31, 2004, provisional application No. 60/899,640, filed on Feb. 6, 2007.

(51) Int. Cl.
*A61B 5/03* (2006.01)
*A61B 5/00* (2006.01)
*A61B 6/00* (2006.01)

(56) References Cited

U.S. PATENT DOCUMENTS

| | | |
|---|---|---|
| 4,689,621 A | 8/1987 | Kleinberg |
| 4,726,381 A | 2/1988 | Jones |
| 4,763,658 A | 8/1988 | Jones |
| 4,765,339 A | 8/1988 | Jones |
| 4,774,955 A | 10/1988 | Jones |
| 4,803,992 A | 2/1989 | Lemelson |
| 4,844,076 A | 7/1989 | Lesho et al. |
| 4,883,063 A | 11/1989 | Bernard et al. |
| 5,003,980 A | 4/1991 | Loo et al. |
| 5,353,807 A | 10/1994 | DeMarco |
| 5,372,133 A | 12/1994 | Hogen Esch |
| 5,395,366 A | 3/1995 | D'Andrea et al. |
| 5,415,181 A | 5/1995 | Hogrefe et al. |
| 5,422,926 A | 6/1995 | Smith et al. |
| 5,604,531 A | 2/1997 | Iddan et al. |
| 5,721,462 A | 2/1998 | Shanks |
| 5,762,612 A * | 6/1998 | Campbell ................. 600/558 |
| 5,778,882 A | 7/1998 | Raymond et al. |
| 5,792,053 A | 8/1998 | Skladnev et al. |
| 5,800,350 A | 9/1998 | Coppleson et al. |
| 5,829,437 A | 11/1998 | Bridges |
| 5,833,603 A | 11/1998 | Kovacs et al. |
| 5,842,977 A | 12/1998 | Lesho et al. |
| 5,853,005 A | 12/1998 | Scanlon |
| 5,993,378 A | 11/1999 | Lemelson |
| 6,134,300 A | 10/2000 | Trebes et al. |
| 6,169,914 B1 | 1/2001 | Hovland et al. |
| 6,173,201 B1 | 1/2001 | Front |
| 6,240,312 B1 | 5/2001 | Alfano et al. |
| 6,254,548 B1 | 7/2001 | Ishikawa et al. |
| 6,317,927 B1 | 11/2001 | Lai et al. |
| 6,324,418 B1 | 11/2001 | Crowley et al. |
| 6,343,227 B1 | 1/2002 | Crowley |
| 6,353,658 B1 | 3/2002 | Trebes et al. |
| 6,368,275 B1 | 4/2002 | Sliwa et al. |
| 6,368,331 B1 | 4/2002 | Front et al. |
| 6,400,974 B1 | 6/2002 | Lesho |
| 6,423,056 B1 | 7/2002 | Ishikawa et al. |
| 6,428,531 B1 | 8/2002 | Visuri et al. |
| 6,428,569 B1 | 8/2002 | Brown |
| 6,440,069 B1 | 8/2002 | Raymond et al. |
| 6,453,199 B1 | 9/2002 | Kobozev |
| 6,567,687 B2 | 5/2003 | Front et al. |
| 6,582,365 B1 | 6/2003 | Hines et al. |
| 6,584,348 B2 | 6/2003 | Glukhovsky |
| 6,607,301 B1 | 8/2003 | Glukhovsky et al. |
| 6,629,776 B2 | 10/2003 | Bell et al. |
| 6,632,175 B1 | 10/2003 | Marshall |
| 6,709,387 B1 | 3/2004 | Glukhovsky et al. |
| 6,719,684 B2 | 4/2004 | Kim et al. |
| 6,764,440 B2 | 7/2004 | Iddan et al. |
| 6,776,165 B2 | 8/2004 | Jin |
| 7,787,926 B2 * | 8/2010 | Kimchy .................. 600/407 |
| 2001/0041835 A1 | 11/2001 | Front et al. |
| 2002/0099310 A1 | 7/2002 | Kimchy et al. |
| 2003/0139661 A1* | 7/2003 | Kimchy et al. .......... 600/407 |
| 2004/0015075 A1 | 1/2004 | Kimchy et al. |
| 2004/0054248 A1 | 3/2004 | Kimchy et al. |
| 2004/0054278 A1 | 3/2004 | Kimchy et al. |
| 2004/0204646 A1 | 10/2004 | Nagler et al. |
| 2004/0250124 A1 | 12/2004 | Chesla et al. |
| 2005/0055174 A1 | 3/2005 | David et al. |
| 2005/0205792 A1 | 9/2005 | Rousso et al. |
| 2005/0266074 A1 | 12/2005 | Zilberstein et al. |
| 2006/0033029 A1 | 2/2006 | Popper |
| 2006/0217593 A1 | 9/2006 | Gilad et al. |
| 2006/0237652 A1 | 10/2006 | Kimchy et al. |
| 2007/0156047 A1 | 7/2007 | Nagler et al. |
| 2010/0174184 A1* | 7/2010 | Kimchy et al. .......... 600/436 |

FOREIGN PATENT DOCUMENTS

| | | |
|---|---|---|
| JP | 2003-325438 | 11/2003 |
| JP | 2003-325440 | 11/2003 |
| WO | WO 00/49958 | 8/2000 |
| WO | WO 01/62134 | 8/2001 |
| WO | WO 02/16965 | 2/2002 |
| WO | 02/26130 A1 | 4/2002 |
| WO | 02058531 | 8/2002 |
| WO | WO 02/058531 | 8/2002 |
| WO | 02/095351 A2 | 11/2002 |
| WO | 03/001966 A2 | 1/2003 |
| WO | WO 2004/042546 | 5/2004 |
| WO | WO 2005/067383 | 7/2005 |
| WO | WO 2005/104939 | 11/2005 |
| WO | WO 2005/112895 | 12/2005 |

OTHER PUBLICATIONS

Gutman G. et al., "A novel needle-based miniature x-ray generating system", Abstract Only, Phys. Med. Biol., 49(20):4677-4688 (2004).
Compton, Arthur H., 1923. "A Quantum Theory of the Scattering of X-Rays by Light Elements". Physical Review 21: 483-502.
Compton, Arthur H., 1923. "The Spectrum of Scattered X-Rays". Physical Review 22: 409-413.
Haga, et al., 2004. "A miniature x-ray tube". Applied Physics Letters 84: 2208-2210.
Madsen, et al., 1989. "Gastrointestinal Transit of Technetium-99m-Labeled Cellulose Fiber and Indium-111-Labeled Plastic Particles". Journal of Nuclear Medicine 30: 402-406.
Proano, et al., 1990. "Transit of solids though the human colon: regional quantification in the unprepared bowel". Am. J. Physiol. 258: G856-G862.
Tartari, et al., 2000. "Compton Scattering Elemental Imaging of a Deep Layer Performed with the Principal Component Analysis". Proc. of the 15th World Conference on Non-destructive Testing, Conservation and Restoration in Art and Architecture, Rome, Oct. 15-21, 2000.
"X-ray contrast medium". Encyclopaedia of Medical Imaging, vol. 1. www.medcyclopaedia.com.
Brochard, et al., 2003. "Estimation of movement parameters of 3D textured surfaces using the autocorrelation function". Pattern Recognition Letters 24: 2031-2045.
Camilleri, et al., 1989. "Human gastric emptying and colonic filling of solids characterized by a new method". Am. J. Physiol. 257: G284-G290.
U.S. Appl. No. 60/531,690.
U.S. Appl. No. 60/559,695.

\* cited by examiner

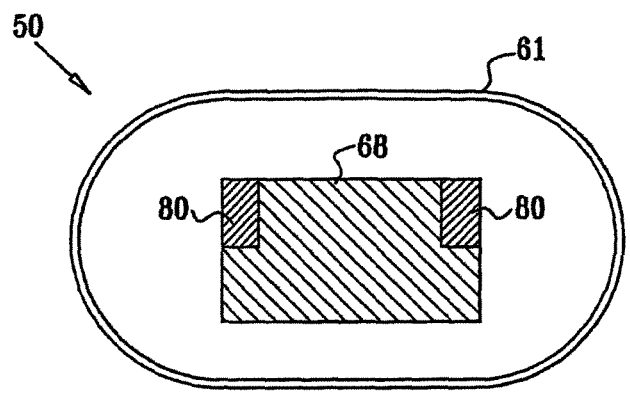
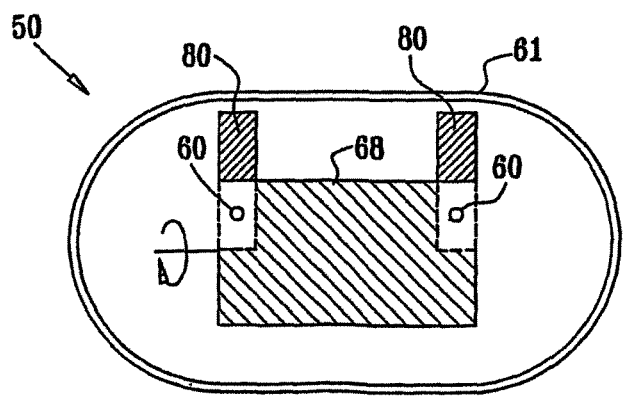

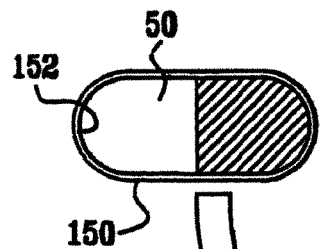
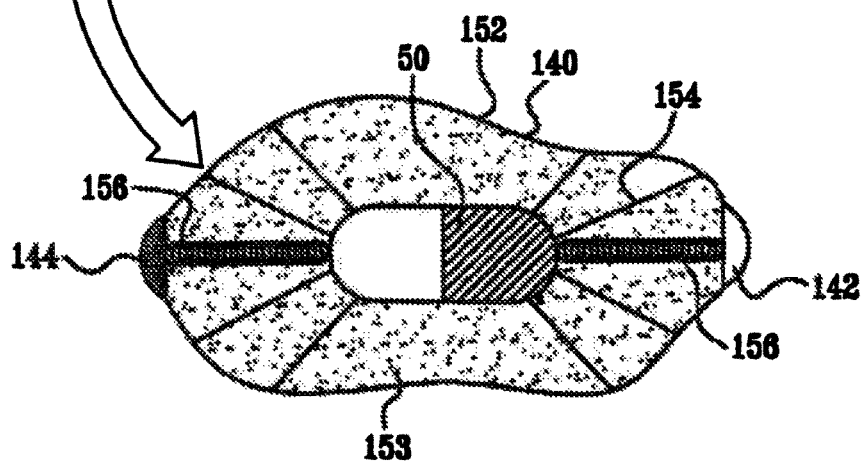
FIG. 9C
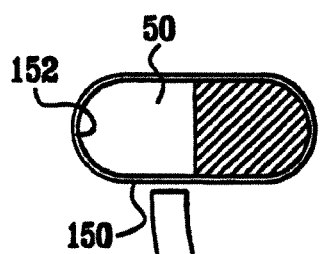
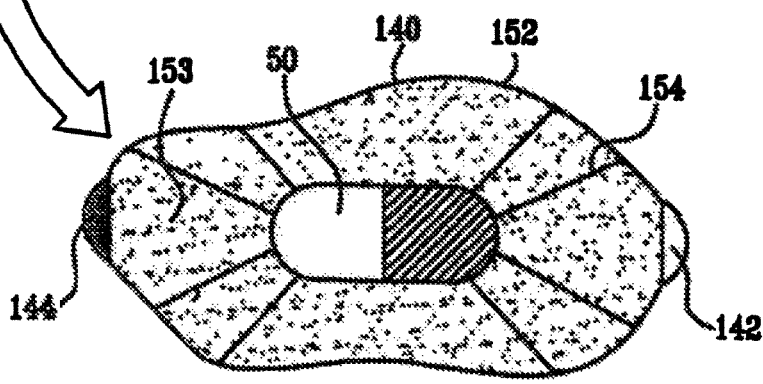
FIG. 9D

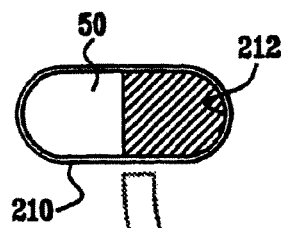
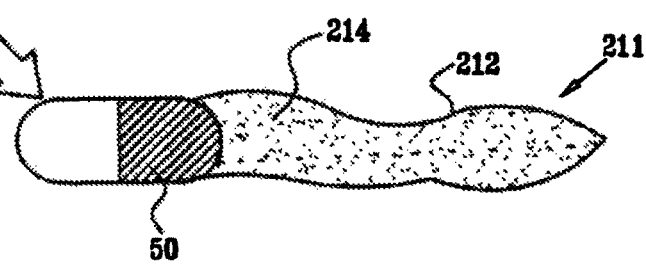
FIG. 11A
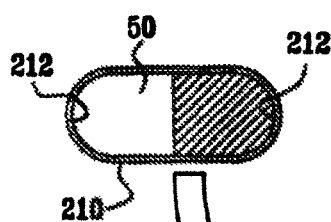
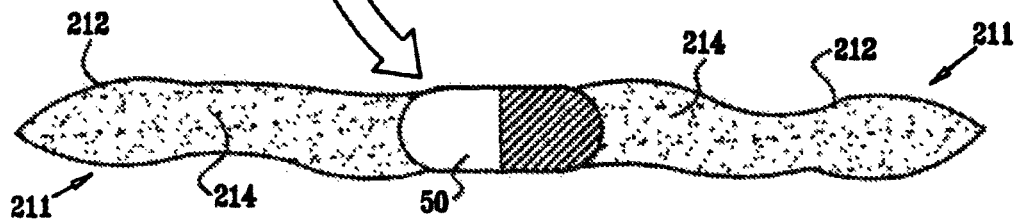
FIG. 11B

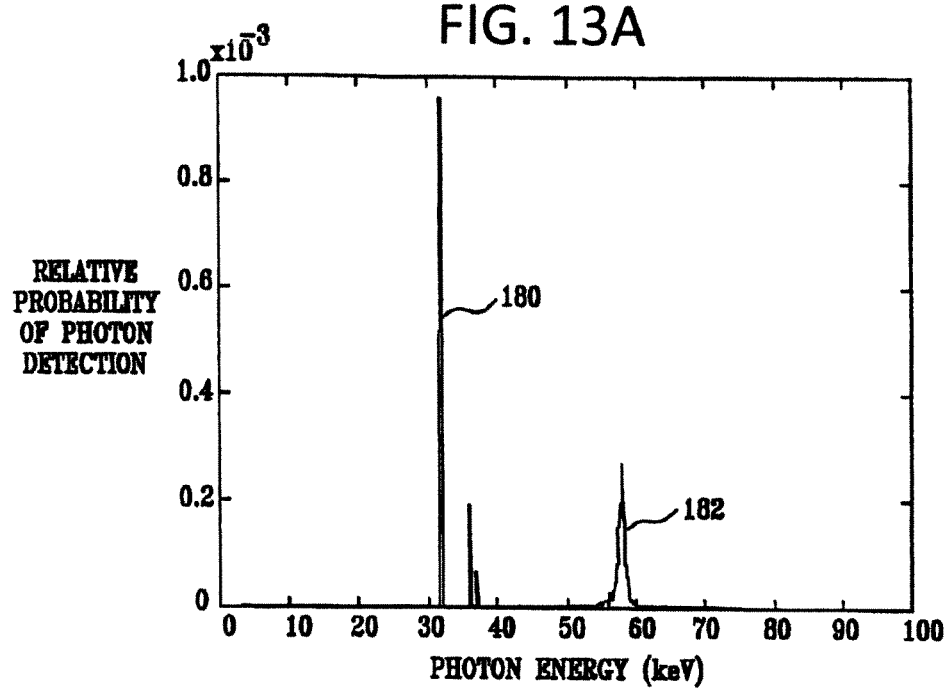
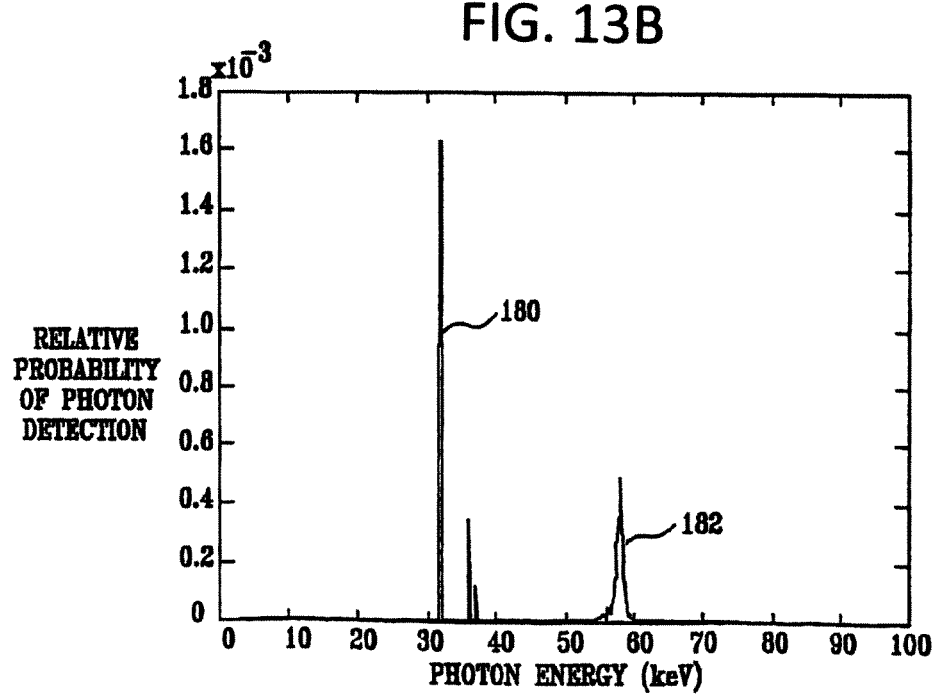

INTRA-LUMEN POLYP DETECTION

CROSS-REFERENCES TO RELATED APPLICATIONS

This application is a continuation-in-part of U.S. patent application Ser. No. 10/596,065, filed May 26, 2006, which is a national phase application of PCT Application Serial No. PCT/IL04/001140, published in the English language as WO 2005/058129, and having an international filing date of Dec. 16, 2004, which claims the benefit of U.S. Provisional Patent Application 60/531,690, filed Dec. 17, 2003, and U.S. Provisional Patent Application 60/559,695, filed Mar. 31, 2004, the contents of which are incorporated herein by reference in their entirety.

This application is also a continuation-in-part of U.S. patent application Ser. No. 12/525,672, filed Aug. 4, 2009, which is a national phase application of PCT Application Serial No. PCT/IL08/000163, published in the English language as WO 2008/096358, and having an international filing date of Feb. 6, 2008, which claims the benefit of U.S. Provisional Patent Application 60/899,640, filed Feb. 6, 2007, the contents of which are incorporated herein by reference in their entirety.

FIELD OF THE INVENTION

The present invention relates generally to the field of detection of conditions of a body lumen, and specifically to a swallowable device that travels in the colon and detects anatomical anomalies.

BACKGROUND OF THE INVENTION

Colorectal cancer is one of the leading causes of death in the Western world. Clinical evidence suggests that early detection of primary colorectal cancer leads to a 90% or better 5-year survival rate, while detection of the disease when it has already metastasized leads to poor prognosis with a 50% or less 5-year survival rate and a 30% recurrence rate. Colorectal cancer frequently begins with the growth of polyps and other clinically-relevant features that may harbor the potential for cancer of the gastrointestinal (GI) tract. Colorectal cancer screening and early detection have a substantial positive impact on the prognosis of this malignancy. Accordingly, there is a need for an improved method and device capable of early detection of polyps and other abnormalities in the GI tract.

SUMMARY OF THE INVENTION

According to one aspect of the present invention, a subject swallows a contrast agent, and, typically after a waiting period, a capsule comprising one or more gamma and/or X-ray radiation sources and radiation detectors. As the capsule travels through the GI tract, the radiation sources "illuminate" the vicinity of the capsule. The GI contents (including the contrast agent), GI wall, and tissue outside of the GI tract act as a scattering media for the emitted radiation, typically primarily through the process of Compton scattering. The scattered photons then travel back through the GI contents, which include the contrast agent. The radiation detectors count appropriately Compton backscattered photons as well as X-ray fluorescence (XRF) photons generated responsively to the emitted radiation. A control unit is adapted to analyze the XRF photons generated responsively to the emitted radiation and Compton backscattered photons generated responsively to the emitted radiation.

The count rates collected by each detector per unit time interval are analyzed, typically only for predetermined photon energy windows. These data are presented to a physician in a manner that enables him to assess the likelihood that there is a polyp or some other anatomical deformation in the GI tract. In some embodiments, the data are also analyzed to indicate a general area of the colon where an abnormality may exist. These polyps or anatomical anomalies may be the result of a tumor beginning to grow within the GI tract. If the physician suspects the presence of a polyp or some other anatomical anomaly that may be cancerous or pre-cancerous, the subject is typically referred for further diagnostic testing, such as colonoscopic examination.

The radiation source in the capsule may have an energy of at least 10 keV, with the photon detector likewise adapted to detect photons in about the same energy range. The radiation source may include a miniature X-ray generator or a radioisotope, emitting gamma rays or X-rays.

In some embodiments, the control unit is adapted to analyze a time derivative of the data in order to generate the information. In some embodiments, the radiation source includes at least one collimator, adapted to collimate the radiation emitted by the radiation source. In some embodiments, the photon detector includes at least one collimator, adapted to collimate the photons detected by the photon detector.

In some embodiments, the control unit is adapted to distinguish between gas in the GI tract and the clinically-relevant feature.

In some embodiments, the capsule includes an acceleration sensor and/or a pressure sensor.

In some embodiments, the apparatus includes an external data-recording unit, adapted to remain outside a body of the subject, and the capsule is adapted to wirelessly transmit information to the data-recording unit while the capsule is in the GI tract.

In some embodiments, the capsule includes an agent-storage reservoir for storing the agent and releasing the agent in an area of clinical interest in the GI tract.

In some embodiments, the data regarding the photons include data for one or more predefined photon energy windows, and the control unit is adapted to analyze the data associated with the one or more predefined photon energy windows.

In an embodiment, the control unit is adapted to estimate a distance from a site of the capsule to a wall of the GI tract. In some embodiments, the control unit is adapted to estimate the distance using an algorithm in which there is an inverse relationship between the distance and a count of the detected photons. In some embodiments, the control unit is adapted to estimate the distance by estimating a depth of the contrast agent between the site of the capsule and the wall of the GI tract responsively to the analysis of the Compton backscattered photons.

In an embodiment, the radiation source is adapted to emit the radiation from the capsule only a portion of a time that the capsule is in the GI tract. In some embodiments, the capsule includes a sensor, adapted to sense a parameter indicative of possible imminent motion of the capsule in the GI tract, and the radiation source is adapted to emit the radiation from the capsule responsively to the sensing of the parameter by the sensor. In some embodiments, the radiation source includes a miniature X-ray generator, configured to emit the radiation only during the portion of the time.

In some embodiments, the radiation source includes a radioisotope, the capsule includes a radiation shield, and the capsule includes an actuator, adapted to move at least one of the radiation source and the shield, such that the shield does not block the radiation emitted from the radiation source during the portion of the time. In some embodiments, the capsule includes a plurality of collimators, and the collimators and the shield are configured such that, at any given time, the radiation emitted by the radiation source passes through less than all of the collimators. In some embodiments, the capsule includes a rod, the radiation source is coupled to the rod, and the actuator is adapted to move the rod in order to move the radiation source. In some embodiments, the capsule includes at least one spring, and the rod and spring are configured to form a mechanical oscillator.

In an embodiment, the capsule includes electrodes coupled to an external surface of the capsule; and a pulse generator, and the control unit is adapted to drive the pulse generator to apply an electrical signal to the colon capable of inducing a mass movement in the colon. In some embodiments, the control unit is adapted to generate the information regarding a geometry of muscles of the colon.

In an embodiment, a plurality of photon detectors are arranged to detect photons arriving from a plurality of respective detection directions. In some embodiments, a plurality of collimators are arranged to emit the radiation in a plurality of respective emission directions corresponding to the detection directions.

In an embodiment, the capsule includes at least one radiation shield. In some embodiments, the at least one shield is configured to prevent radiation from being emitted from the radiation source in directions other than a single confined solid sector relative to a sphere surrounding the capsule.

In an embodiment, the radiation source is adapted to emit radiation having a primary plurality of energy levels, and the control unit is adapted to analyze counts of photons having a secondary plurality of energy levels, different from the primary plurality of energy levels. In some embodiments, the radiation source is adapted to emit radiation having first and second energy levels, and the control unit is adapted to analyze a mathematical relationship between (a) a count of the photons detected by the photon detector having a third energy level and (b) a count of the photons detected by the photon detector having a fourth energy level. In some embodiments, the relationship includes a ratio of (a) the count of the photons having the third energy level to (b) the count of the photons having the fourth energy level, and the control unit is adapted to analyze the ratio. In some embodiments, the control unit is adapted to analyze the relationship to determine an actual, calibrated distance between a site of the capsule and a wall of the GI tract.

In an embodiment, the control unit is adapted to analyze Compton backscattered photons generated responsively to the emitted radiation and having an energy level indicative of a backscattering angle of 180°± a range parameter that is less than 30°, e.g., less than 20°, or less than 10°.

In an embodiment, the control unit is adapted to detect that the capsule has reached an area of clinical interest within the GI tract, for example, by detecting and analyzing XRF photons. Alternatively or additionally, the capsule may include a pH-sensitive element, and the control unit is adapted to detect that the capsule has reached the area responsively to change in pH in the area that affects the pH-sensitive element. The capsule may also include a pressure sensor, and the control unit is adapted to detect that the capsule has reached the area responsively to a change in pressure detected by the pressure sensor, potentially in combination with signals from Compton backscattering and XRF.

In an embodiment, the control unit is configured to initiate rotation of the collimator in response to detecting that the capsule has reached an area of clinical interest within the GI tract.

In an embodiment, the collimator is rotatable with respect to the housing through at least 270°.

In an embodiment, the collimator includes two or more rotatable collimators, each of which collimators is rotatable with respect to the housing through less than 360°.

In an embodiment, the photon detector is configured to rotate with respect to the housing and to detect photons generated responsively to the emitted radiation. In an embodiment, the detector is rotatable through at least 270°. In an embodiment, the detector includes two or more rotatable detectors, each of which detectors is rotatable with respect to the housing through less than 360°.

In an embodiment, the capsule includes at least one extending element, adapted, when extended, to maintain the capsule at least a certain distance from or with a certain orientation relative a wall of the GI tract. In some embodiments, the extending element is configured to extend when the capsule reaches an area of clinical interest within the GI tract. In some embodiments, the extending element includes at least one leg-shaped element, an expandable ring structure, and/or an unfolding element. The extending element may include an expandable flexible chamber In some embodiments, the flexible chamber may include a super-absorbent hydrogel, and the flexible chamber is adapted to expand when the hydrogel absorbs liquids from the GI tract.

In an embodiment, the control unit is adapted to analyze incident photons having a same energy as the radiation emitted by the radiation sources. In some embodiments, the control unit is adapted to analyze both the incident photons and Compton backscattered photons having an energy level indicative of a backscattering angle of 180°± a range parameter that is less than 30°. In some embodiments, the apparatus includes more photon detectors than radiation sources.

In some embodiments, radio frequency (RF) transmission and reception is used to measure if the capsule is moving, and/or to detect a rate of movement of the capsule. In other embodiments, low voltage pulse transmission and reception is used to measure if capsule is moving and/or to detect a rate of movement of the capsule. In some embodiments, the capsule and/or external data-recording unit runs an adaptive algorithm to optimize the frequency of the scanning. The algorithm works by evaluating the differences in readings for all imaged sectors of the colon as a function of time.

BRIEF DESCRIPTION OF THE DRAWINGS

The following figures depict certain illustrative embodiments of the invention in which like reference numerals refer to like elements. These depicted embodiments are to be understood as illustrative of the invention and not as limiting in any way.

FIGS. 3A and 3B are schematic illustration of a capsule having shield wings in accordance with an embodiment of the present invention;

FIG. 9A-9E are schematic illustration of the capsule of the system of FIG. 1 coupled to an inflatable balloon, in accordance with an embodiment of the present invention;

FIGS. 11A-C are graphs showing experimental results measured in accordance with an embodiment of the present invention;

FIGS. 13A-D show actual experiment results from the experiment performed using the tank of FIG. 12, in accordance with an embodiment of the present invention.

DETAILED DESCRIPTION OF EMBODIMENTS

Figure 1:
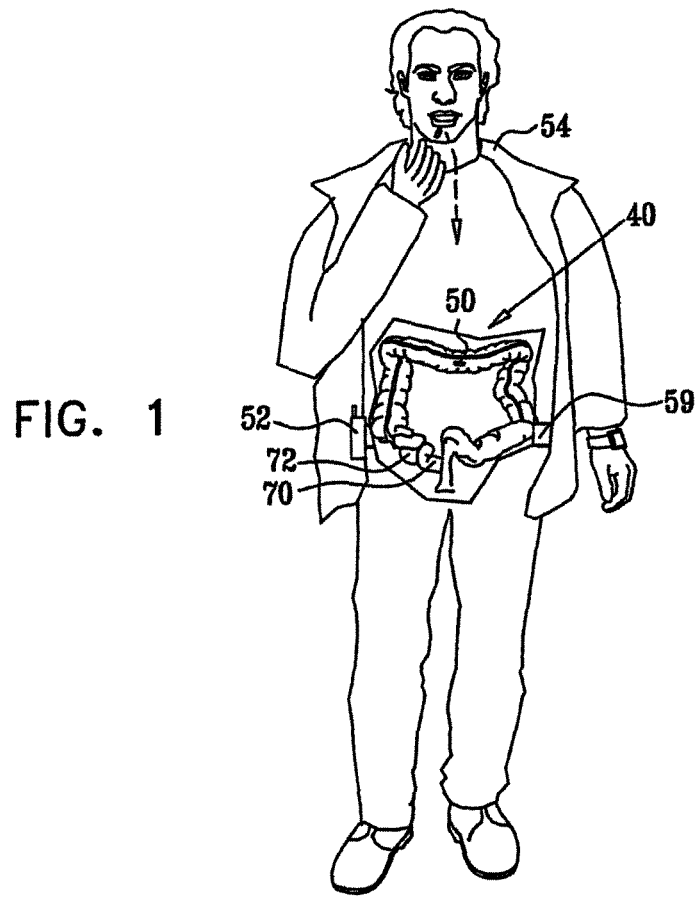
FIG. 1 is a schematic illustration of a screening system for screening a GI tract in accordance with an embodiment of the present invention.

Reference is made to FIG. 1, which is a schematic illustration of a screening system 40 for screening a GI tract 72 of a subject 54, in accordance with an embodiment of the present invention. System 40 typically comprises an ingestible capsule 50 and an external data-recording unit 52. For some applications, data-recording unit 52 is worn on a belt 59 around the subject's waist or elsewhere on the subject's body, such as the wrist (not shown). Alternatively, for some applications, the data-recording unit may be inside the capsule 50, obviating the need for an external data-recording unit 52. In these applications, the data recorded by capsule 50 are retrieved after the capsule has been expelled from the body. In a typical screening procedure using system 40, an oral contrast agent 70 is administered to the subject. Contrast agent 70 is typically adapted to pass through the GI tract and be expelled with the feces, substantially without being absorbed into the blood stream. After the contrast agent is administered (e.g., several hours after the contrast agent is administered), subject 54 swallows capsule 50.

Figure 5:
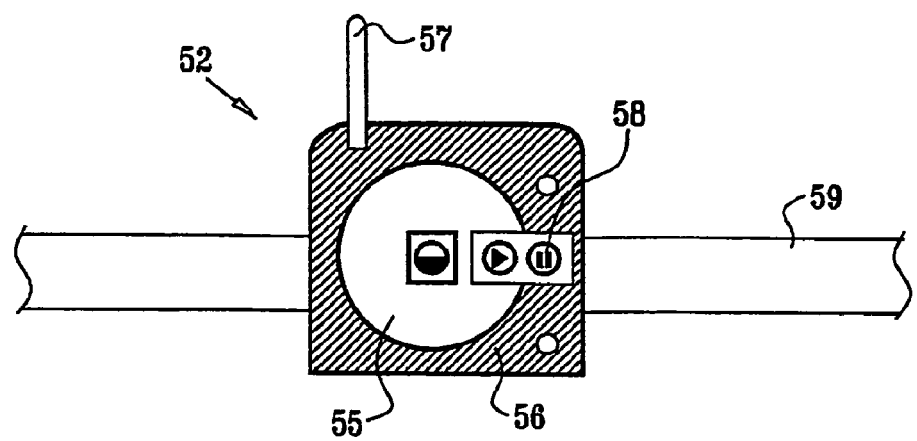
FIG. 5 is a schematic illustration of an external data-recording unit of the system of FIG. 1.
Figure 6A:
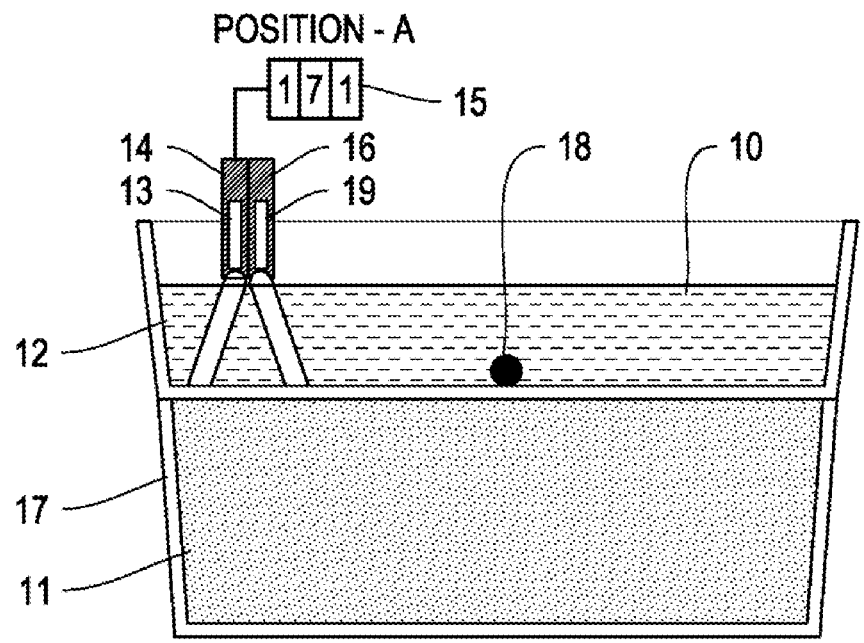
FIGS. 6A-6D are schematic illustrations of apparatus for conducting an exemplary experiment that illustrates physical principles upon which some embodiments of the present invention are based.
Figure 6B:
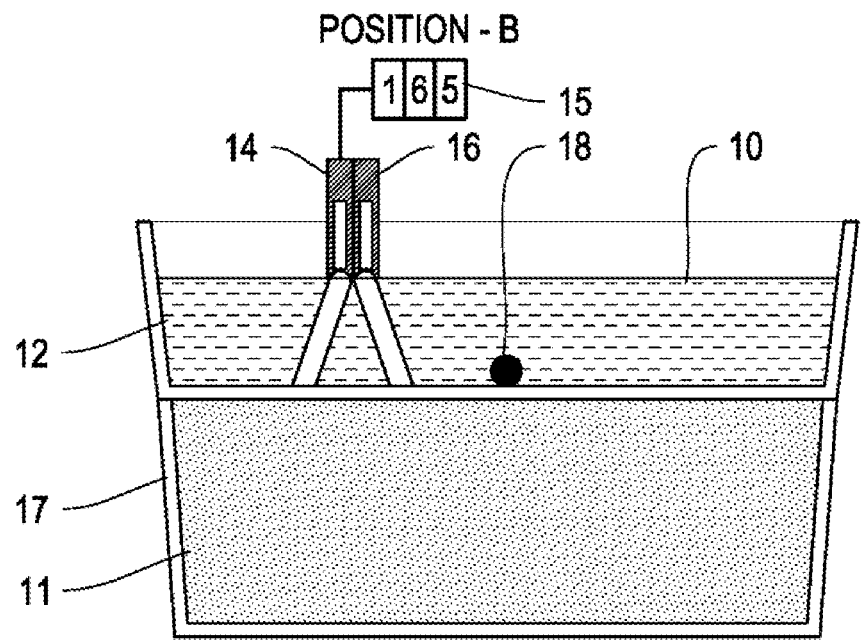
Figure 6C:
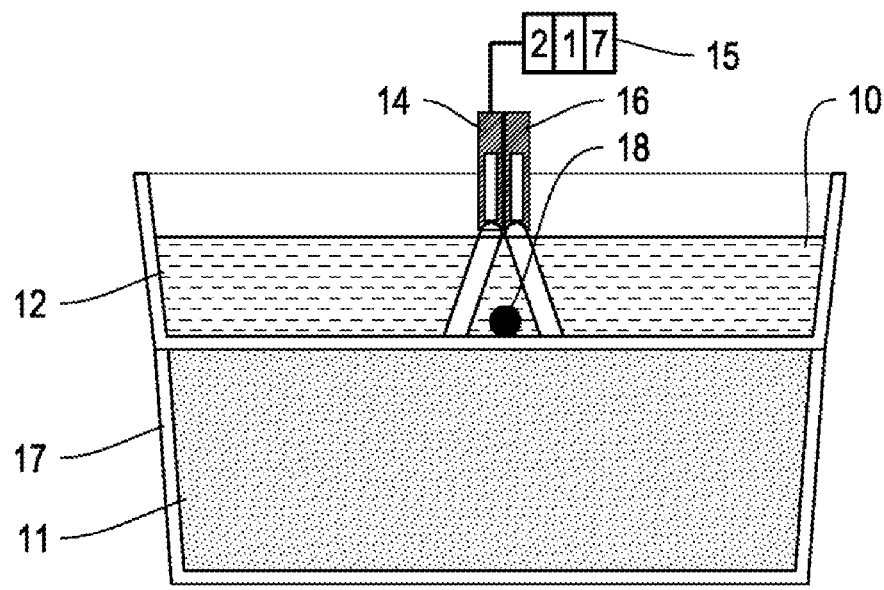
Figure 6D:
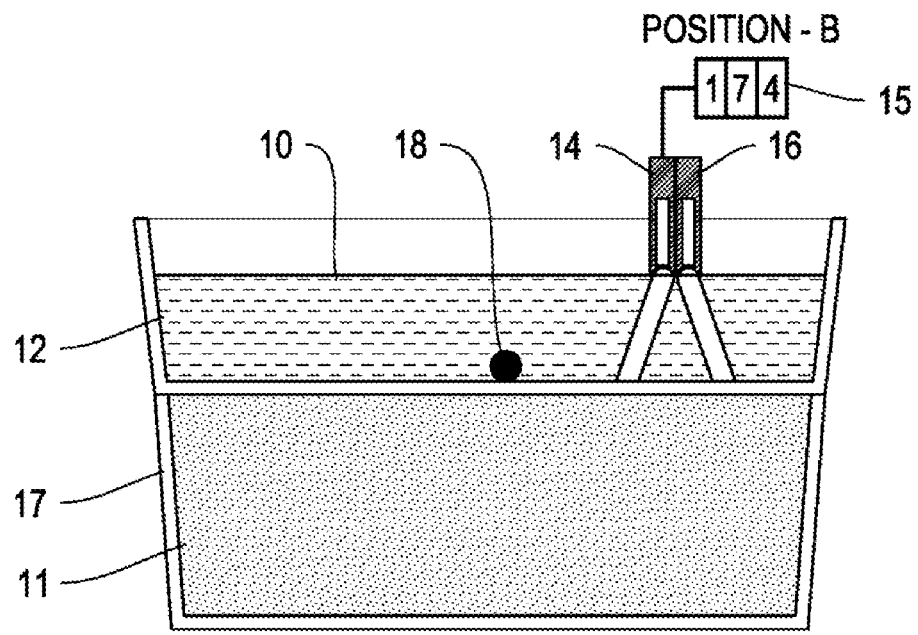

Reference is made to FIG. 5, which is a schematic illustration of an exemplary external data-recording unit 52 in accordance with an embodiment of the present invention. Data-recording unit 52 comprises a receiver/memory unit 55, a support electronics/battery unit 56, an antenna 57, and user controls 58. Unit 52 also typically comprises a strap 59, such as a belt or wrist/arm strap, for coupling the unit to subject 54.

Figure 2:
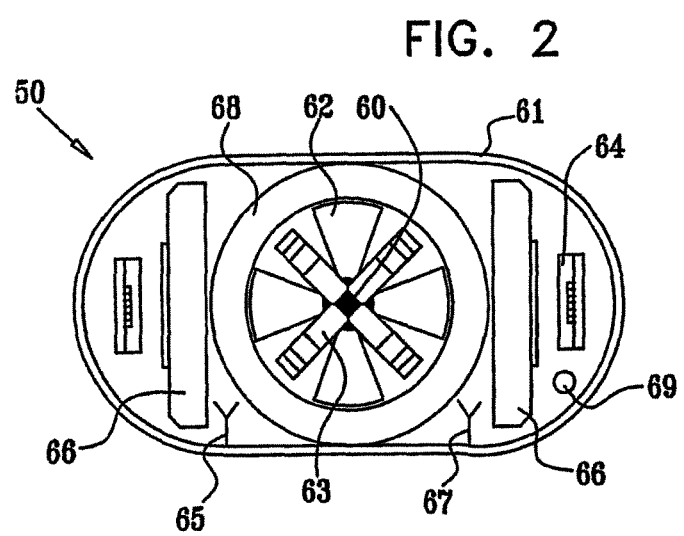
FIG. 2 is a schematic illustration of a capsule of the system of FIG. 1.

Turning now to FIG. 2, which is a schematic illustration of capsule 50, in accordance with an embodiment of the present invention. Capsule 50 comprises at least one radiation source 20 adapted to emit gamma and/or x-rays (i.e., radiation having an energy of at least 10 keV), the source being disposed in a housing' 21. Alternatively or additionally, radiation source 20, and/or an additional radiation source disposed within the capsule, emits beta radiation. Capsule 50 further comprises at least one gamma and/or or x-ray radiation detector 22, and, typically, at least one collimator 23 adapted to collimate the radiation produced by radiation source 20. Alternatively or additionally, detector 22, and/or an additional detector disposed within the capsule, is adapted to detect backscattered beta particles, and/or electrons generated in response to radiation emitted from source 20. For some applications, radiation source 20 comprises a radioisotope. Alternatively, radiation source 20 comprises a miniature radiation generator. Capsule 50 also typically comprises electronic circuitry 24, a power supply 26 (such as a battery), a wireless communication device for communicating with external data-recording unit 52, and a radiation shield 28. In some embodiments, the capsule comprises a pressure sensor 29. As appropriate for various applications, the wireless communication device may comprise electronic devices 25 and 27, which may comprise antennae or electrodes.

Typically, shield 28 is configured to shield the subject from emitted radiation when the capsule is not scanning the GI tract. In embodiments in which beta radiation is emitted from the capsule, the shield typically comprises a high-density ceramic material to stop electrons and at the same time to reduce secondary "stopping radiation" x-rays from being generated. In addition, a combination of a ceramic shield and a high atomic number metal shield on its outer perimeter may be used to reduce emission of secondary x-rays. Secondary x-rays are the result of Compton interaction of photons coming from source 20 through collimator hole 23 and hitting the capsule housing. Some of the photons from the Compton interaction on this surface return in the direction of detectors 22 and may be detected. In some embodiments, shield 28 reduces the number of photons reaching the detectors following this interaction.

Figure 7:
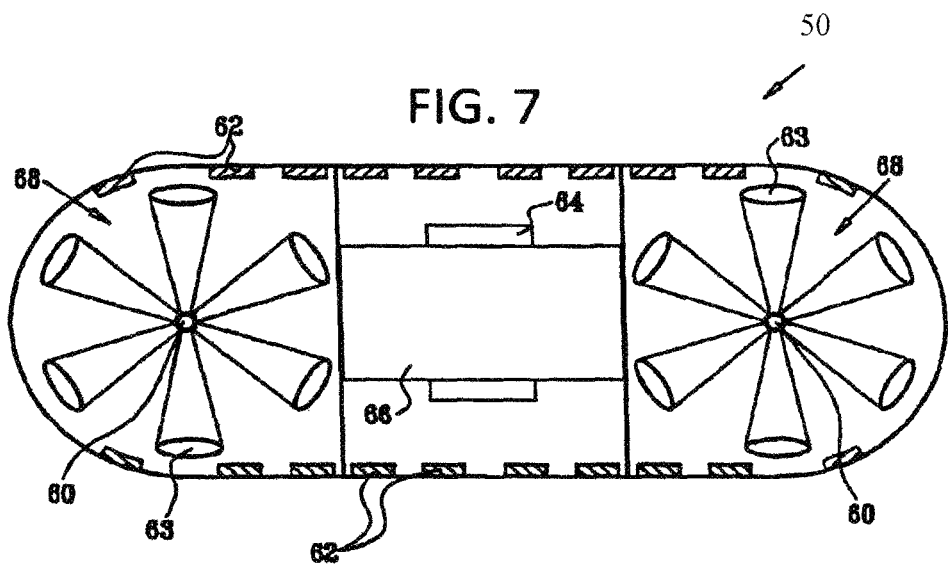
FIG. 7 is a schematic illustration of one configuration of the capsule of the system of FIG. 1 in accordance with an embodiment of the present invention.

Reference is made to FIG. 7, which is a schematic illustration of one configuration of capsule 50, in accordance with an embodiment of the present invention. In this embodiment, capsule 50 comprises one or more radiation sources 60, one or more collimators 63, adapted to collimate radiation generated by radiation sources 60; and one or more radiation detectors 62, which are typically only slightly collimated or not collimated at all. Radiation sources 60 thus illuminate a confined solid sector (relative to the capsule). This is typically achieved by providing respective shields 68 for radiation sources 60, which prevent photons from being emitted in directions other than the preferred sector for each source. Shields 68 typically comprise a material having a high atomic weight and high specific density, such as lead, tungsten, or gold. Other arrangements for the sources, detectors and collimation may also be used, as appropriate, such as a cylindrical, spherical or other shield casing with the one or more sources.

In an embodiment of the present invention, a single source is placed within a spherical capsule, and the shell of the capsule is shaped such that multiple respective columns of photons outputted from the source are detected by one or more detectors on the surface of the capsule. In this embodiment, the detectors are typically not collimated.

In an embodiment of the present invention, radiation source 60 comprises a miniature X-ray generator, which may be used for radiation source 60 instead of a radioisotope to illuminate the colon contents with X-ray photons. Turning such a generator on and off as needed typically reduces exposure of the subject to radiation. In addition, the energy range can be better controlled and the flux may be higher for the on periods without increasing subject total exposure.

Figure 8:
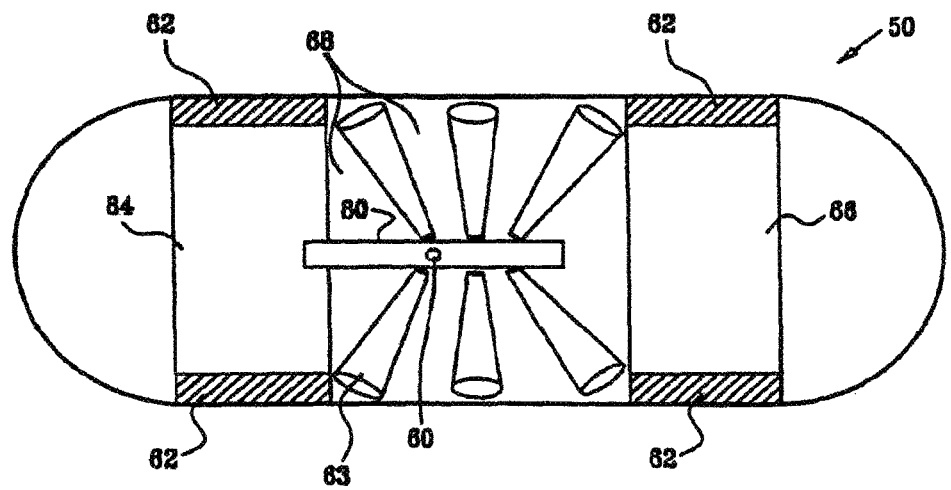
FIG. 8 is a schematic illustration of a time-multiplexed configuration of the capsule of the system of FIG. 1 in accordance with an embodiment of the present invention.
Figure 9A:
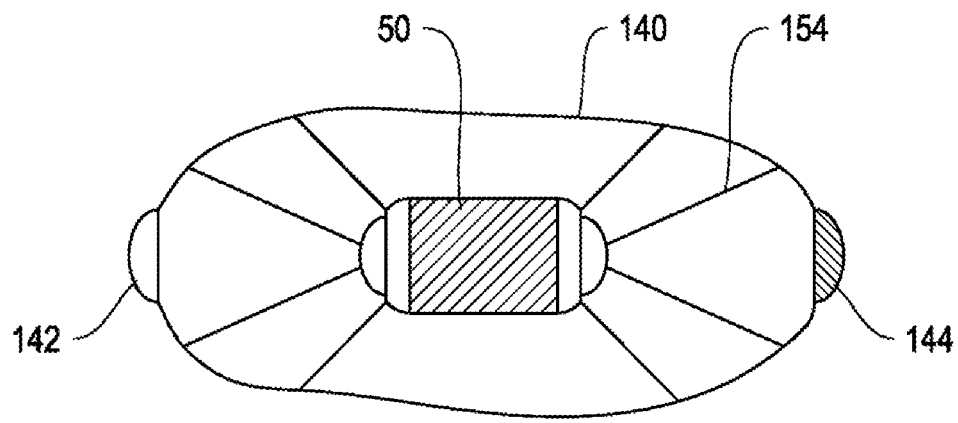
Figure 9B:
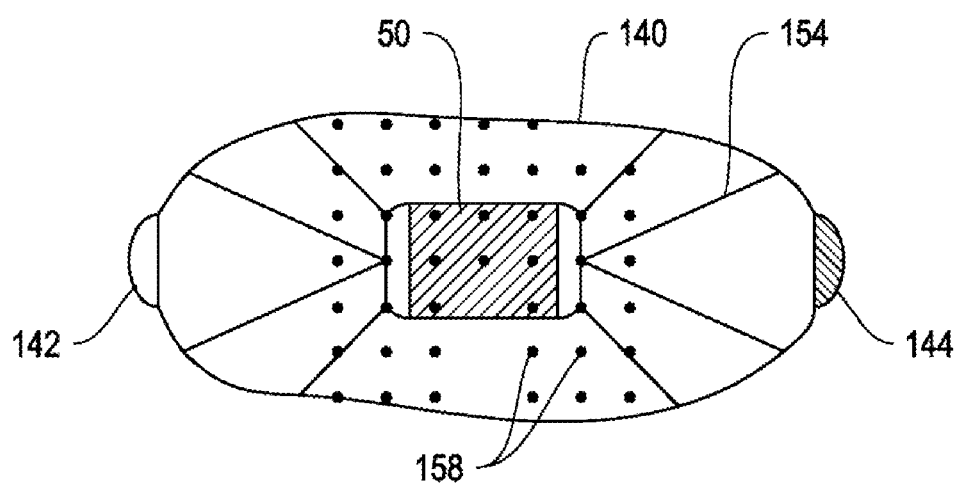
Figure 9E:
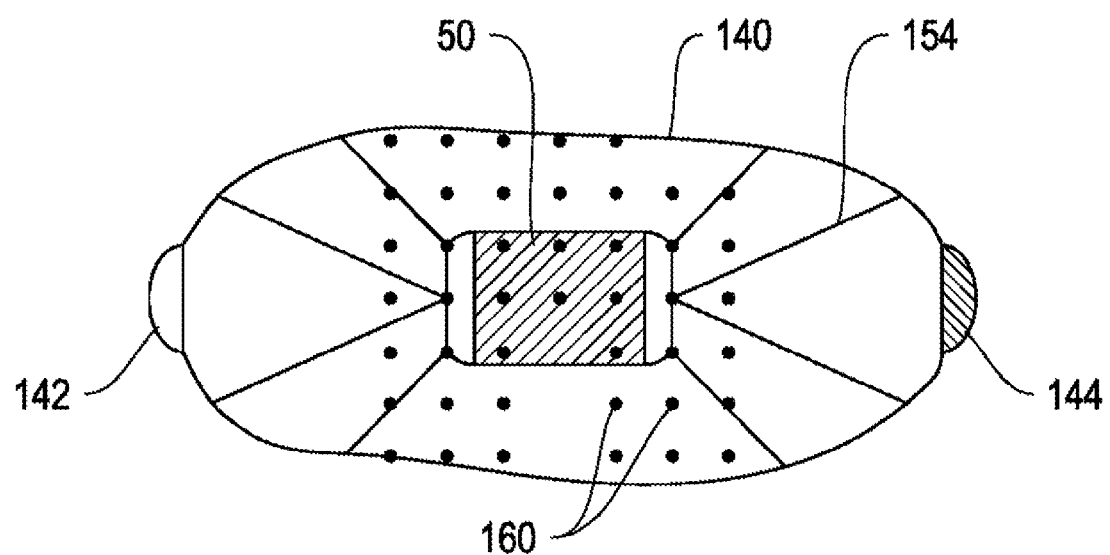

Reference is made to FIG. 8, which is a schematic illustration of a time-multiplexed configuration of capsule 50, in accordance with an embodiment of the present invention. In this embodiment, capsule 50 comprises at least one radiation shield 68. The capsule is configured such that shield 68 blocks radiation emitted from radiation source 60 a portion of the time that the capsule is in the GI tract. In some embodiments, this partial blocking is achieved by moving shield 68. Alternatively or additionally, the blocking is achieved by moving radiation source 60. In some embodiments, radiation source 60 is coupled to a moving rod 80. During a rest phase, at times when the capsule is not intended to gather data, radiation source 60 is positioned behind shield 68 so that the amount of radiation that escapes towards the subject's body is minimal. During an operational phase, during which capsule 50 gathers data, rod 80 is moved back and forth, such as by a low power actuator 84 (for example, a voice coil linear actuator, or a piezoelectric linear actuator motor). The motion of rod 80 exposes radiation source 60 to different collimators 63, causing radiation source 60 to illuminate, at different times, different angular sectors of the sphere surrounding the capsule. Detectors 62 detect the Compton backscattered photons or the X-ray fluorescence photons from the colon contents including media, time-synchronized to the radiation source position.

In some embodiments, radiation source 60 comprises an isotope, e.g., Tl201, I111, I131, Ga67, Tc99m, or Pd 100. In some embodiments, rod 80 comprises a heavy metal, such as tungsten, lead, or tantalum. In some embodiments, shield 68 comprises a high Z material, such as tungsten, gold, or tantalum.

Using these techniques, the system resolution may be controlled by adjusting the "illumination" volumes. For example, a relatively high intensity radiation source may be placed in a capsule, and by controlling the collimation angle of the source, enable a very narrow high resolution observed volume. In this configuration, the overall radiation exposure for the subject is still relatively small.

The physiology and anatomy of the human colon is such that most of the time (during an average period of 24-72 hours) the contents of the colon are stationary, mixing a little from time to time but not moving forward. Once every few hours, a contraction starts that generates pressure within the colon (up to an average of 200 mmHg) squeezing material forward towards the anus. To minimize subject radiation exposure, the motorized back-and-forth movement of radiation source 60 is typically only activated when the capsule senses intra-lumen pressure buildup indicative of imminent mass movement within the colon, and/or when the capsule senses angular change, using the MEMS acceleration sensor chip, indicative of possible imminent motion of the capsule. During periods in which the capsule does not sense any pressure or change in tilt angle, and the XRF readings for the detector(s) closest to the colon wall are at steady state, radiation source 60 is stationary at the center of shield 68.

The motorized back-and-forth movement of radiation source 60 causes the radiation source to emit gamma or X-ray radiation through collimators 63 as the radiation source passes back and forth behind shield 68. Collimators 63 are arranged such that at any given time only a predetermined subset of the collimators emit radiation. Exposing the radiation source only when the capsule is expected to collect data generally reduces the amount of radiation to which the subject is exposed.

In an embodiment of the present invention, actuator 84 and rod 80 are arranged such that rod 80 moves according to the dynamics of a forced mechanical oscillator. In this arrangement, rod 80 is coupled to at least one spring (spring not shown) such that the combination of the rod and spring forms a mechanical oscillator having a specific resonance frequency. At or near this frequency, the energy required to move rod 80 is minimal. Actuator 84 supplies the energy lost to friction. At both ends of the movement of the rod, the rod slows. The rod, spring, and collimators are typically arranged such that the radiation source is exposed to the openings of the collimators at the locations at which the rod slows.

In some embodiments of the present invention, radiation source 60, collimator 63, radiation shield 68, radiation detectors 62 and/or electronic circuitry 64 rotate during scanning. For example, the collimator and/or the detector may rotate through more than 270°, e.g., through 360°.

In some embodiments, as pressure sensor 69 senses changes of pressure related to contractions of the colon muscles, the capsule starts scanning by opening collimator 63 and exposing radiation source 60. Subsequently, radiation shield 68 and radiation detectors 62 start turning at a rate that is typically between 2 and 50 turns per second or, for some applications, between 50 and 500 turns per second. As each collimator 63 allows emission of gamma or x-ray photons to a specific angular sector, radiation detector 62 which turns together with the collimator detects the Compton backscattered photons, x-ray fluorescence photons, and/or electrons returning from the colon contents within that angular sector. In some embodiments, as the rotating portion of the capsule turns, it enables scanning of the whole circumference around the capsule, as the capsule moves forward due to the colon contents movement induced by the colon wall's contractions. In some embodiments, the radial scanning resolution of the capsule is varied by varying a rate of rotation of the rotatable portions of the capsule, and/or by varying the time interval over which the photon flux is integrated, per angular sector. For example, if, for each angular sector, the photon flux is integrated over a larger time period, then each angular sector will be greater, and there will be fewer angular sectors per rotation of the capsule.

For some applications, the capsule comprises a plurality of detectors. Each of the detectors rotates through less than 360°, but the plurality of detectors scans 360°. For example, the capsule may comprise two detectors, each of which can rotate through 180°, such that in combination the two detectors are able to scan 360°. Alternatively or additionally, the capsule comprises a plurality of collimators 63. Each of the collimators rotates through less than 360°, but the plurality of collimators scans 360 degrees. For example, the capsule may comprises two collimators each of which can rotate through 180°, such that in combination the two collimators are able to allow exposure of radiation source 60° to the 360° circumference of the colon.

For some applications, a part of the capsule rotates as described while the other part is generally stationary. For example, the stationary part may include a motor (not shown), a power supply (such as battery 66), pressure sensor 69 and/or a tilt sensor (not shown). For some applications, the transfer of signals and supply current from the stationary part of the capsule to the rotating part of the capsule is done via a slip ring, configured to transfer data signals and supply current. In some embodiments, a rotational encoder is incorporated into the capsule, to enable the electronic circuitry and the capsule software to track the rotational position of the rotating part of the capsule as it rotates. This allows the circuitry to associate each detected photon with its appropriate angular sector. For some applications, the rotational encoder is built into the slip ring by way of a non-continuous conducting surface on the slip ring divided into even sections (typically 4-128 sectors), that enable the electronic circuit to detect the position of the rotating slip ring as it turns. In some embodiments, the encoder comprises a marker, such as a missing sector position, in order to mark the completion of a 360° turn. For example, this may enable the electronics to resynchronize every turn, thus compensating for rotational speed variations or errors in the position detection.

For some applications, capsule 50 scans the colon at pre-defined time intervals to ensure scanning of the entire colon even when the capsule is moving very slowly and pressure changes are not sensed. For example, the capsule may scan the colon every 5-30 seconds, and/or every 30 seconds to 5 minutes.

For some applications, radiation shield 68 is set to open collimators 63 only when the capsule senses movement of the capsule, for example, in response to pressure sensor 69 detecting pressure changes in the colon. In this manner, scanning of the colon and the exposure of the patient to radiation is generally limited to only those periods when the colon contents are moving, thus reducing the overall radiation exposure for the patient. In some embodiments, this saves power consumption, as scanning is done only when the capsule senses pressure changes.

In some embodiments, in response to capsule 50 detecting a pressure change indicative of a bowel movement, the capsule scans continuously as rapid movement through the colon is anticipated. Typically, in response to sensing a pressure change, the capsule scan continuously for a period of between 10 seconds and one minute, or between one minute and ten minutes. In some embodiments, movement of the capsule is detected using other sensing means.

In some embodiments, radio frequency (RF) transmission and reception is used to measure if capsule 50 is moving, and/or to detect a rate of movement of the capsule. For this, the capsule transmits a short RF pulse from electronic device 65 (e.g., an antenna) every few seconds, typically every 1-60 seconds, and receives the signal from electronic device 67 (e.g., another antenna), which is located at a different location on the capsule. If the capsule moved in the last time interval, then the received signal will have different amplitude. Due to the low impedance and high attenuation of the colon contents, any change in the relative position of the capsule in the colon alters the RF signal.

In some embodiments, low voltage pulse transmission and reception is used to measure if capsule 50 is moving and/or to detect a rate of movement of the capsule. For this, the capsule generates low frequency voltage pulses between two or more electronic devices 65 and 67 (e.g., electrodes) every few seconds, typically every 1-60 seconds, located at different locations on the capsule. If the capsule moved in the last time interval, the current induced by the voltage pulses will have different amplitude due to the changes in impedance caused by changes in the relative position of the capsule in the colon.

In some embodiments, a magnetic flow meter, as is known in the art, is used to measure a rate of movement of capsule 50. Typically, a small magnet is placed close to or on the surface of capsule 50, and a magnetic field is applied across the colon. Two or more electrodes measure a voltage induced by movement of the magnet across the applied magnetic field. A rate of movement of the capsule is deduced from the strength of the induced voltage.

In some embodiments, capsule 50 and/or external data-recording unit 52 runs an adaptive algorithm to optimize the frequency of the scanning. The algorithm works by evaluating the differences in readings for all imaged sectors of the colon as a function of time. In an embodiment, the algorithm maintains a record of a given number of scan readings (e.g., the count rate of Compton backscattered photons for each of the given number of scan readings) for each sector, and calculates the average for these past sectors. Then, the algorithm compares the current reading with this average. If the difference between the square of the average and the current reading is below a lower threshold, the next reading is set to be taken following a longer time interval than the previous time interval. Typically, there is a maximum time interval beyond which the time interval is not extended. If the difference between the square of the average and the current reading is greater than an upper threshold, the next reading is taken following a shorter time interval than the previous time interval. If the difference between the square of the average and the current reading is between the upper and lower thresholds, then the time interval until the next reading is taken is kept constant.

In some embodiments, the adaptive algorithm evaluates the differences in pressure readings as a function of time. For example, the algorithm may maintain a record of a few past pressure readings, and calculate the average and standard deviation for these past time pressure measurements. Then, the algorithm compares the current pressure reading with this average, and if the difference of the square of the average and the new reading is larger than a certain threshold, the capsule starts scanning, or scans at a higher rate than it was scanning previously. In some embodiments, the threshold is adaptively set based on the average of the past few readings and the standard deviation of these readings. Typically, the capsule begins scanning in response to detecting a pressure that is one to ten standard deviations, or a given value plus one to ten standard deviations, greater than the average of the given number of previous readings.

In some embodiments, respective images are generated in response to data detected by radiation detector 62. The adaptive algorithm is used to detect movement, and/or a rate of movement of the capsule by comparing respective images to each other. In some embodiments, the adaptive algorithm is applied in response to the capsule detecting a change in pressure. Typically, the algorithm varies the time interval between successive scans of the capsule in response to detecting movement and/or a rate of movement of the capsule. In some embodiments, the algorithm constructs an image that is the average of the previous several images; thereafter the algorithm compares the current image to the average image. Typically, the algorithm varies the time interval between successive scans of the capsule in response to detecting movement and/or a rate of movement of the capsule. In some embodiments, the algorithm is initiated in response to the pressure sensor detecting a change in pressure.

In an embodiment of the present invention, a tilt sensor is employed in a stationary part of the capsule to monitor the 3D tilt angle of the capsule, relative to the earth's center of gravity. This information is used by the capsule to sense turning while scanning in order to readjust the frame of reference during post processing. This information is typically transmitted from the capsule to external data-recording unit 52.

In some embodiments, data regarding the tilt angle of the capsule, pressure changes of the capsule, and/or acceleration of the capsule are used to identify when the capsule is expelled from the subject's anus. Typically, in response to detecting the expulsion of the capsule, data from the capsule are immediately transmitted to external data-recording unit 52.

In some embodiments, radiation source 60 emits beta radiation, and the emitted high-energy electrons interact directly with the colon contents, tissue of the colon wall, and tissue outside the colon. The electrons are scattered by these interactions, and a portion of the electrons backscatter at various energy levels, and are detected by detector 62. The emitted electrons typically have an energy of greater than 1 mega-electron volt (MeV), e.g., between 1.5 and 7 MeV. For example, the emission of primarily beta radiation, rather than of gamma and/or x-ray radiation, may allow the use of less radiation, because electrons interact with matter with higher probability than do photons. Furthermore, beta radiation has a maximum range which depends on the energy of the electrons. For example, the electrons emitted by Y-90 have a maximum range of 11 mm in water. Therefore, exposure to radiation is limited, such that tissue outside the colon has limited or no radiation exposure.

For some applications, electron backscattering is used to sense small changes in tissue densities near capsule 50. This, in turn, is used to differentiate between a) tubular and villous polyps and b) neoplastic polyps. Tubular and villous polyps typically have a higher density than do neoplastic polyps. Tubular and villous polyps are more likely than neoplastic polyps to become cancerous. In some embodiments, the emitted beta radiation generates electrons and/or XRF photons in the colon.

In some embodiments of the invention, electrons and/or photons generated in response to beta radiation are detected and used to quantify the density of the tissue that is close to the capsule. This information can be useful for physicians to classify polyps as either a) tubular or villous, or b) neoplastic.

In some embodiments, radiation source 60 emits beta radiation and also gamma and/or x-ray radiation. For example, the beta radiation may be used for detection at close ranges from the capsule with high sensitivity, whereas the gamma and/or x-ray radiation may be more sensitive for longer ranges from the capsule. In such embodiments, detector 62 typically detects backscattered electrons as well as backscattered Compton photons and XRF photons. In some embodiments, the capsule contains a first radiation source that emits photons, and an additional source that emits beta radiation. In some embodiments, the capsule contains a first radiation detector that detects photons, and an additional detector that detects beta radiation. In some embodiments of the present invention, Compton backscatter generated in response to emitted x-ray and/or gamma photons is used to quantify the density of the tissue that is close to the capsule. This information can be useful for physicians to classify polyps as either a) tubular or villous, or b) neoplastic.

In some embodiment of the present invention, Compton backscatter and XRF photons generated in response to emitted x-ray and/or gamma photons, are used to quantify the density of the tissue that is close to the capsule. Typically, this is accomplished by correlating the variations in XRF photon flux with variations in Compton backscattering photon flux, as described in the paragraph below.

Variations in Compton backscattering photon flux which are not correlated with corresponding variations in x-ray fluorescence photon flux are interpreted to indicate changes in tissue density. This may be used to classify polyps as a) tubular or villous, or b) neoplastic.

In response to the radiation emitted by source 60, XRF photons are typically only emitted from the colon contents, which contain contrast agent 70. Compton backscattered photons are emitted from the colon contents as well as from the tissue of the colon walls and beyond. Therefore, in some embodiments, the XRF photon flux is normalized and then subtracted from the Compton photon flux, to enable an automatic evaluation of the photon flux that is related to the tissue of the colon and beyond. Typically, the difference between the normalized XRF photon flux and the Compton photon flux is mainly due to the tissue of the colon, since Compton photon flux is proportional to the square root of the distance from the capsule to the tissue surface. Compton photon flux is further dependent on the density of the tissue. Therefore, by analyzing the Compton photon flux, an automated algorithm provided by some embodiments of the present invention determines the density of the tissue from which the Compton photons were backscattered.

Reference is now made to FIGS. 3A-B, which are schematic illustrations of radiation shield 68 of capsule 50 comprising shield wings 80, in accordance with an embodiment of the present invention. In an embodiment of this invention, when the capsule is not scanning the GI tract, the shield wings are closed (as shown in FIG. 3A), and the subject is shielded from radiation source 60. To initiate scanning of the GI tract, radiation source 60 is exposed by rotating shield 68 together with the detectors 62, so that centrifugal force acts on shield wings 80 causing them to open and expose source 60 (as shown in FIG. 3B). When not rotating, shield wings 80 are typically held closed using a spring. The rotating shield wings are disposed within housing 61 of capsule 50, to avoid contact between moving parts of the capsule and the wall of the colon. In other embodiments, other techniques are employed to move shield 68 and/or source 60 (e.g., by activation of a solenoid).

Figure 4A:
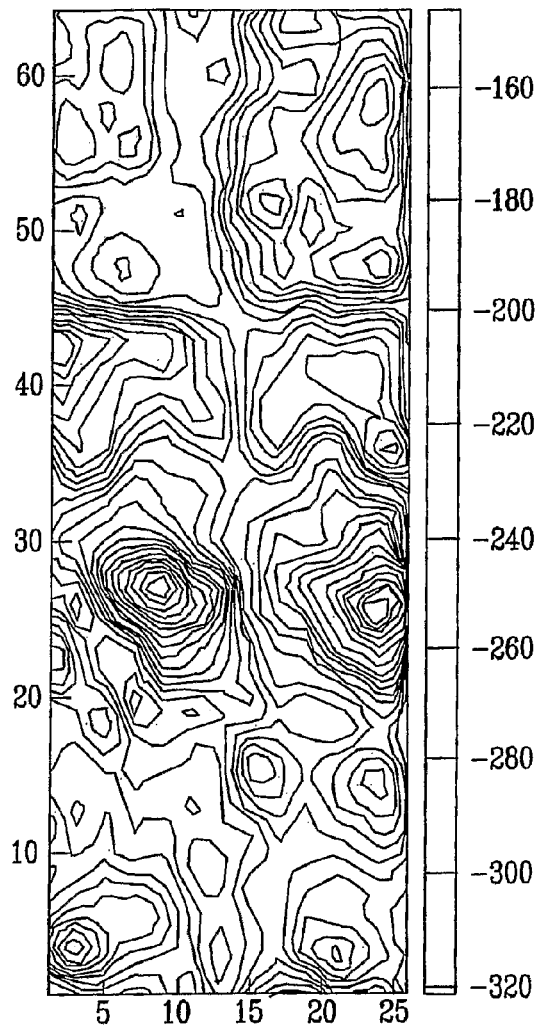
FIGS. 4A and 4B are contour plots indicating the height of features in the GI tract detected with a capsule in accordance with an embodiment of the present invention.
Figure 4B:
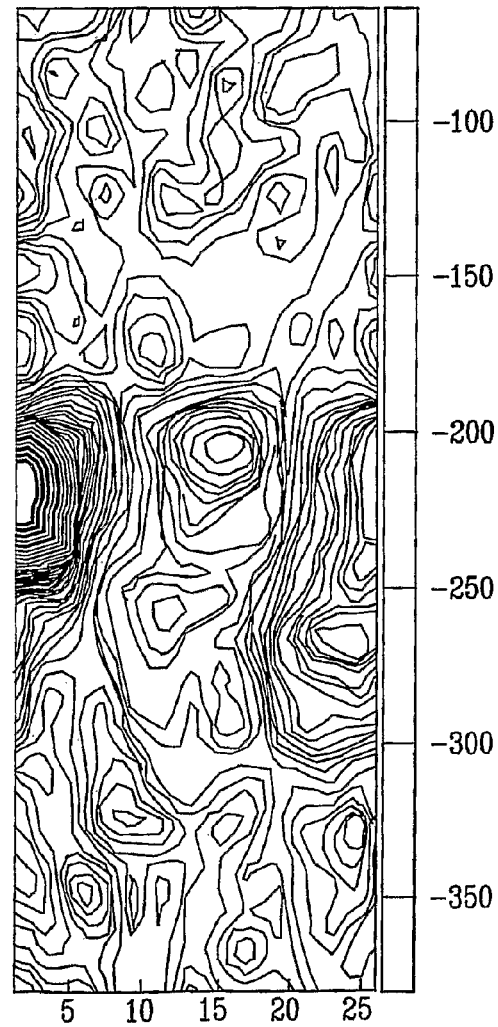

Reference is now made to FIGS. 4A-B, which are height maps of respective polyps which were induced in the colons of respective first and second pigs, the height maps having been generated in accordance with an embodiment of the present invention. In some embodiments of the invention, a processing algorithm is employed to distinguish between polyps with stalks and polyps without stalks. The algorithm typically relies on the fact that the capsule is very likely to contact any polyps larger than a few millimeters (e.g., larger than 6 mm), since the colon walls contract in order to push the capsule forward. This contact with the polyp causes the polyp to align along the path of the capsule, hence stretching the polyp along the longitudinal axis of the colon as the capsule travels near the polyp. This stretching of the polyp reveals the stalk of the polyp to the capsule as it passes the polyp. The stretching of the polyp typically generates asymmetry in the image of the polyp, as the center of the polyp is dragged in the direction of the capsule's movement.

FIG. 4A is a height map of a flat polyp that was induced in the colon of a first pig, the map having been generated using apparatus described hereinabove. FIG. 4B is a height map of a polyp with a stalk induced in the colon of a second pig. A difference can be observed in the shape of the respective height maps, the map of FIG. 4B having an elongated tail associated with the polyp with the stalk. The direction of motion of the capsule was upward on the page, and, the polyp was dragged in that direction. In some embodiments, the likelihood that a polyp is potentially cancerous is assessed by determining if the polyp has a stalk. (Clinical studies of polyps and their progress to cancer suggest that those with stalks are less likely to become cancerous, whereas polyps without stalks—flat polyps—are more likely to become cancerous.)

In some embodiments of the invention, a distance between the capsule and the wall of the colon at any given point is estimated. In addition, the size of a polyp or any other structure within the colon is estimated. To enable these estimations, the flux of XRF and the flux of Compton backscattered photons are measured simultaneously in a large number of measurements throughout the colon, and these values are recorded for post-processing. The concentration of contrast agent typically varies along the colon. Furthermore, XRF photon flux and Compton photon flux both vary in relation to the contrast agent concentration. Therefore, by detecting XRF and Compton backscattering data along the colon, it is possible to estimate the actual distance between the capsule and the wall of the colon, and the actual size of features in the colon. This is done by simultaneously solving equations relating XRF and Compton photon flux to two unknowns, distance and the contrast agent concentration.

For x-ray fluorescence (XRF), the equation that describes the distance between the capsule and the wall of the colon, as a function of photon flux detected, is:

$$LxTf = KxTf * [Ln(Ixrf)/(-\mu xrf * p)]$$

where Lxrf is the estimated distance between the capsule and the colon wall, Kxrf is a known scalar constant, Ixrf is the XRF photon flux which is measured, µxrf is the known XRF interaction probability, and p is the contrast agent concentration.

For Compton backscattering (COMP), the equation that describes the distance between the capsule and the colon wall, as a function of photon flux detected, is:

$$Lcomp = Kcomp * (Ln(I-Icomp)/-\mu comp * p),$$

where Lcomp is the estimated distance between the capsule and the colon wall, Kcomp is a known scalar constant, Icomp is the Compton photon flux which is measured, µcomp is the known Compton interaction probability, and p is the contrast agent concentration.

Since at any point along the colon, these two estimations represent the same true distance, the two equations can be solved simultaneously as there are only two unknowns, namely the true distance L between the capsule and the colon wall and the contrast agent concentration (p). The simultaneous equations to be solved are:

$$L = Kxrf * [(Ln(Ixrf)/(-\mu xrf * p)] \quad \text{(Equation 1)}$$

$$L = Kcomp * [Ln(I-Icomp)/(-\mu comp * p)] \quad \text{(Equation 2)}$$

The colon is divided into sections called haustra. Typically, within each haustrum, the contrast agent concentration remains approximately constant. The concentration of the contrast agent typically changes between adjacent haustra. Typically, the length of each haustrum is 20 mm to 40 mm. In some embodiments, multiple measurements are taken within each haustrum to provide the average contrast agent concentration for that haustrum. Typically, the simultaneous equations provided hereinabove, are solved, for each haustrum, using the average XRF and Compton photon flux readings taken from a plurality of positions (e.g., 2 to 20, or 20 to 40 readings) within the haustrum (e.g., positions within a section of the colon that is 20 mm to 40 mm in length). Within each haustrum, the contrast agent can be assumed not to have changed substantially, and the simultaneous equations using the average photon fluxes are solved to provide the average contrast agent concentration for that haustrum. Typically, equations 1 and 2 are then solved to provide the distance of the capsule from the colon wall, for each of the individual readings within the haustrum, using, for the contrast agent concentration, the average contrast agent concentration of the haustrum.

In some embodiments, a moving average of, for example, 2 to 20, or of 20 to 40, readings of the XRF and Compton photon flux is calculated, for every 20 mm to 40 mm of the length of the colon. For each average Compton and XRF photon flux, a standard deviation of the average is calculated. Typically, the standard deviation of the average photon flux changes when the capsule moves from one haustrum to the next. In some embodiments, an algorithm determines a set of averaged readings that corresponds to readings taken within the same haustrum by detecting a change in the standard deviation of the moving averaged readings. The average contrast agent concentration within that haustrum is then determined by solving, for that haustrum, the simultaneous equations disclosed hereinabove.

Figure 6E:
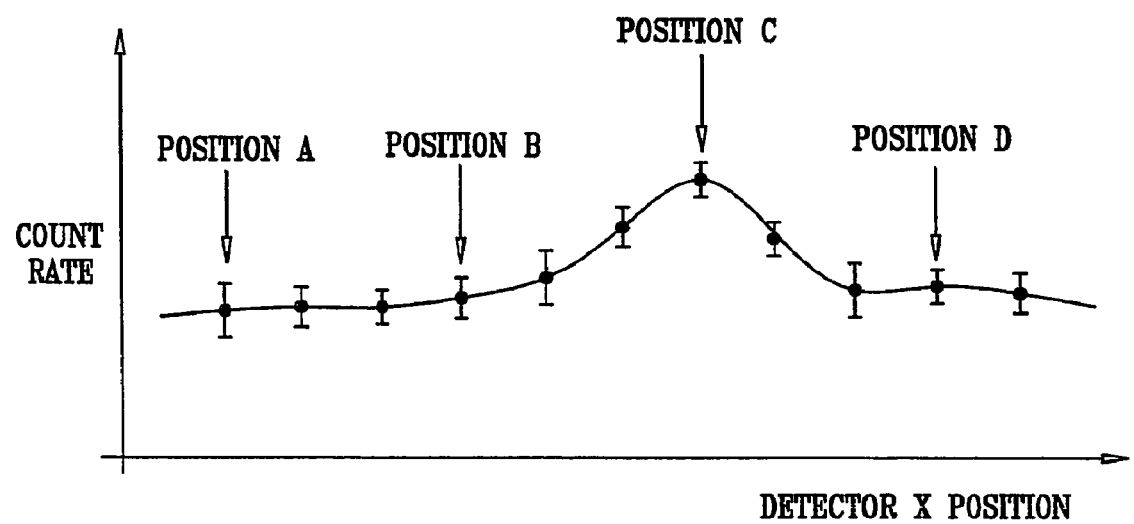
FIG. 6E is a graph showing exemplary experiment results of the experiment of FIGS. 6A-6D.

FIGS. 6A-6D are schematic illustrations of apparatus for conducting an exemplary experiment that illustrates physical principles upon which some embodiments of the present invention are based. FIG. 6E is a graph showing exemplary experiment results of the experiment of FIGS. 6A-6D. Details of the experiment and the analysis of the data are described in copending U.S. patent application Ser. No. 10/596,065, which is incorporated herein by reference.

Figure 10A:
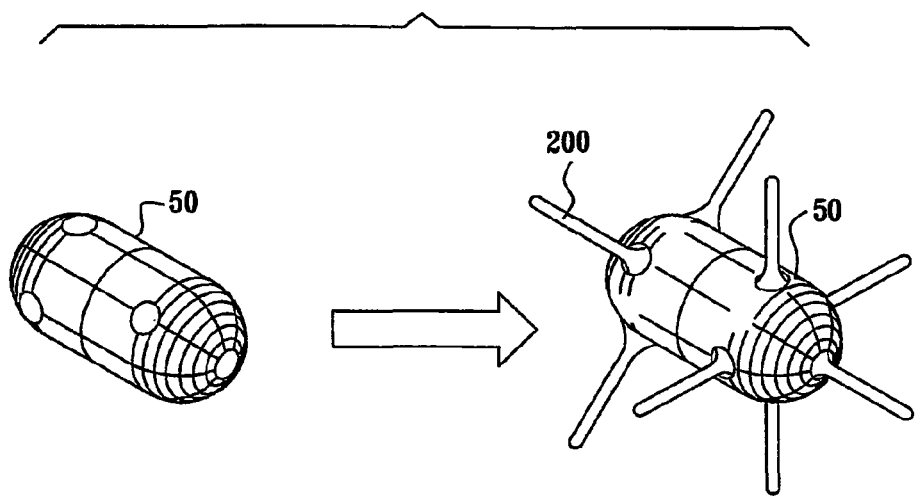
FIG. 10A is a graph illustrating the results of a simulation of the use of an algorithm for estimating distances, in accordance with an embodiment of the present invention.
Figure 10B:
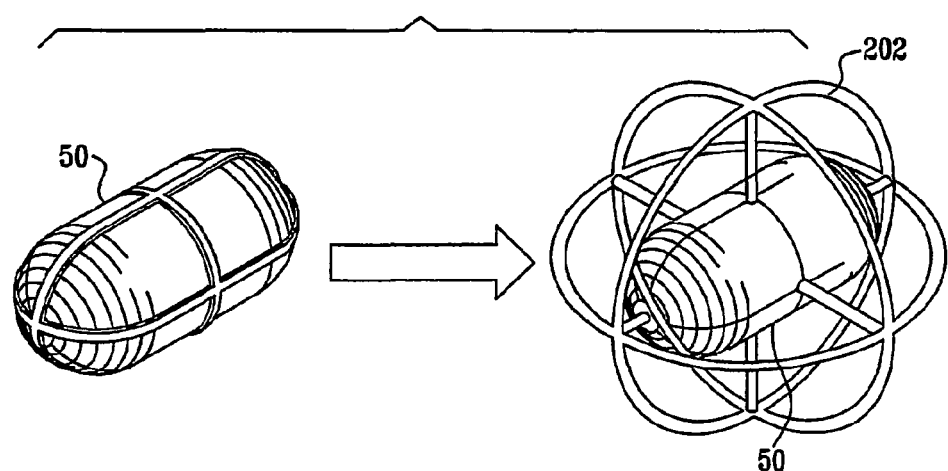
FIG. 10B is a graph illustrating the accuracy of the algorithm of FIG. 10A in the presence of varying percentages of Poisson noise, in accordance with an embodiment of the present invention.

FIGS. 9A to 9E are schematic illustrations of capsule 50 coupled to an inflatable balloon 140; FIGS. 10A and 10B, which are schematic illustrations of a of capsule 50 with extending elements 200, which are deployed when capsule 50 reaches an area of diagnostic interest in the GI tract, typically the colon.

Figure 11C:
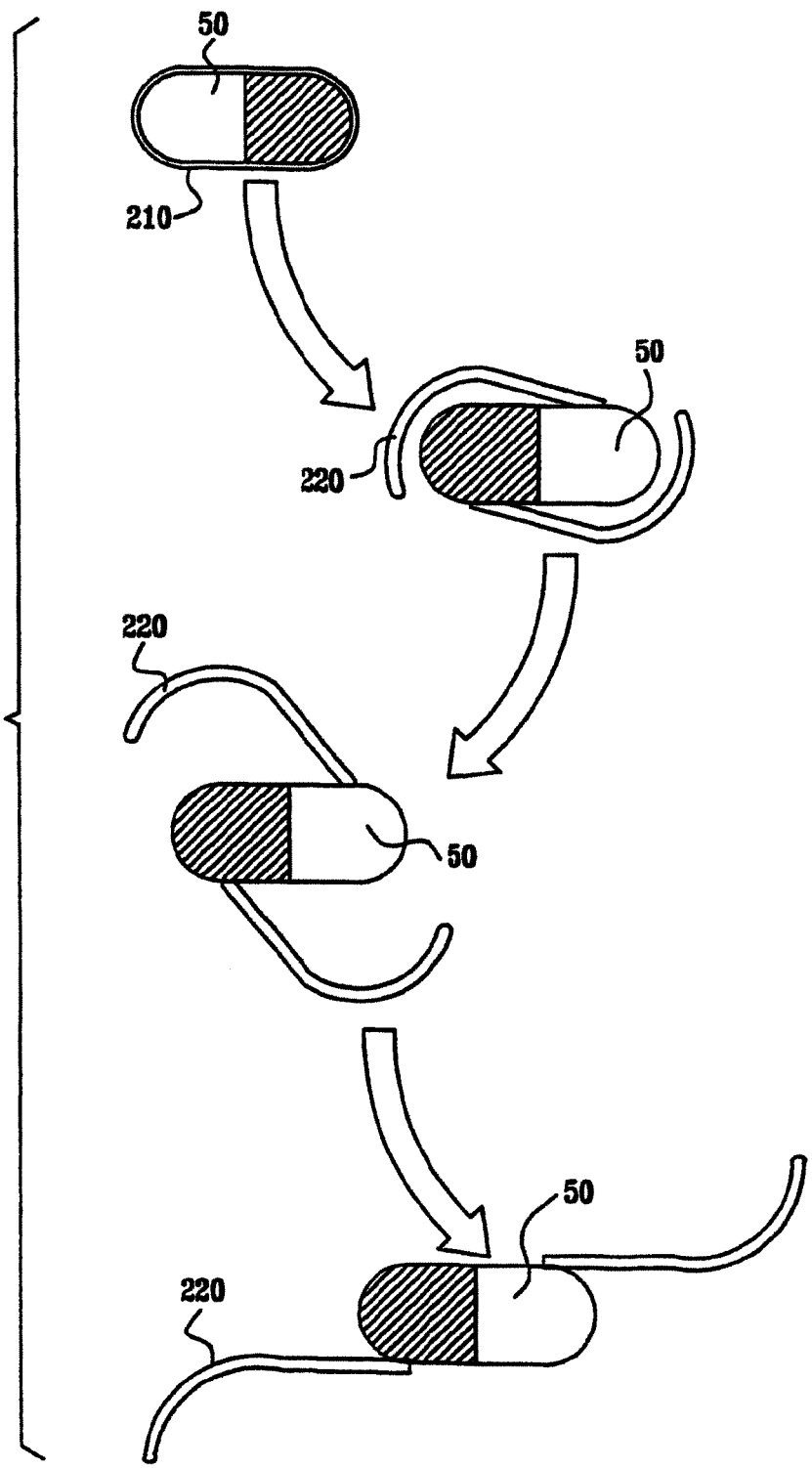

FIGS. 11A and 11B are schematic illustrations of additional extending elements implemented as one or two expandable flexible chambers 211, coupled to one end of capsule 50 (FIG. 11A) or both ends of the capsule (FIG. 11B). Each chambers 211 comprises a semi-permeable expandable membrane 212, which surrounds a super-absorbent hydrogel 214. In alternative embodiments, FIG. 11C shows an embodiment, where the extending elements comprise unfolding elements 220. The embodiments illustrated in FIGS. 11A to 11C have been described in copending U.S. patent application Ser. No. 10/596,065, which is incorporated herein by reference.

Figure 12A:
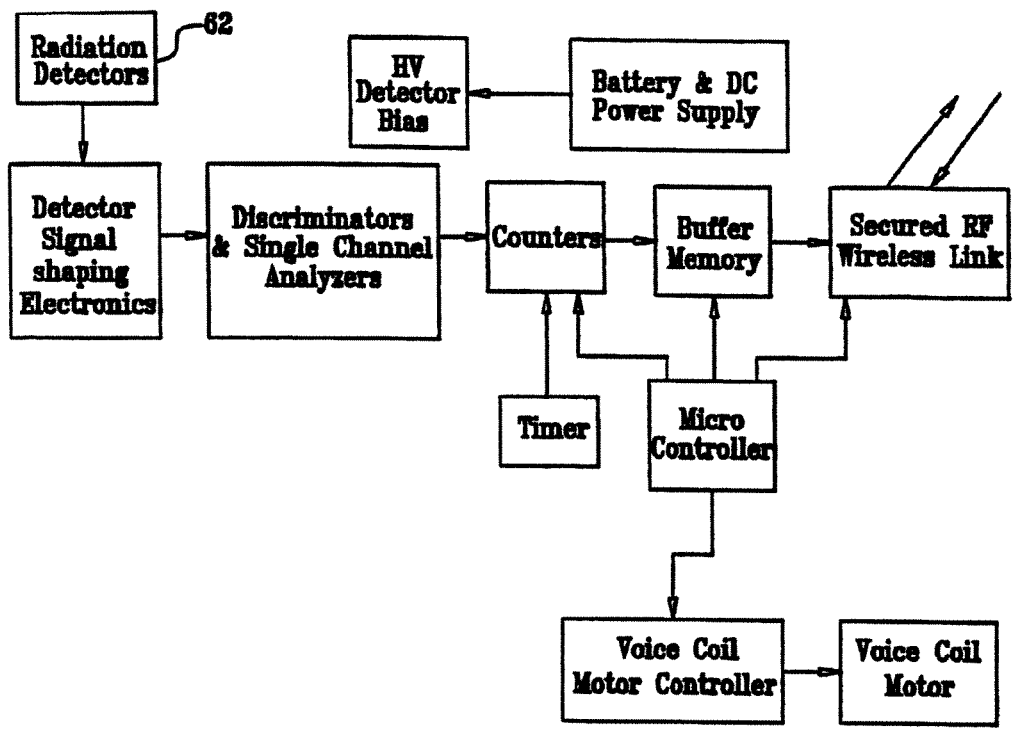
FIG. 12A is a block diagram schematically illustrating various functional blocks of capsule, in accordance with an embodiment of the present invention.

FIG. 12A, which is a block diagram schematically illustrating various functional blocks of capsule 50, in accordance with an embodiment of the present invention. In this embodiment, capsule 50 comprises one or more of the following components: (a) gamma and/or X-ray radiation detectors 62, which may comprise, for example, CZT crystals or scintillation crystals attached to photodiodes; (b) analog signal amplification circuits; (c) digital signal processing circuits; (d) digital memory circuits; (e) RF transmitting, receiving, and support circuitry; (f) calibration supporting circuitry; (g) internal timing circuitry; (h) a MEMS acceleration sensor chip and supporting circuitry; (i) a pressure sensor and supporting circuitry; (j) power supply circuitry including HV bias for the radiation detectors, and voltages for the MEMS; (k) a RF transmitter; (l) a RF receiver; (m) analog circuitry; (n) digital circuitry; and (o) a battery or some other power source, internal or external to the capsule.

Figure 12B:
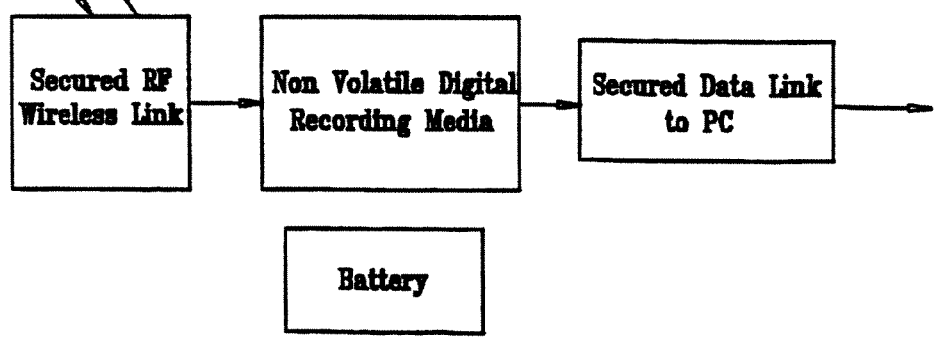
FIG. 12B is a block diagram schematically illustrating various functional blocks of data-recording unit, in accordance with an embodiment of the present invention.

FIG. 12B is a block diagram schematically illustrating various functional blocks of data-recording unit 52, in accordance with an embodiment of the present invention. In this embodiment, data-recording unit 52 typically comprises one or more of the following components: (a) RF communication circuitry; (b) non-volatile digital memory or other recording media adapted to safely store the received data; (d) communication circuitry for transferring the data to a computer; and (e) a power unit and supporting circuitry.

Figure 13C:
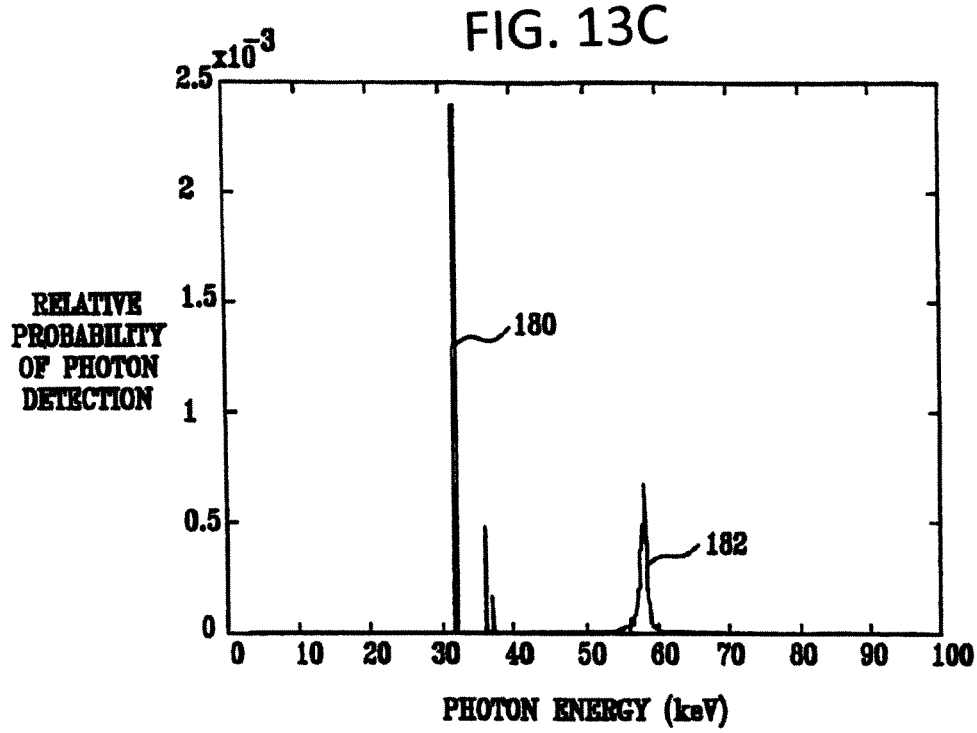
Figure 13D:
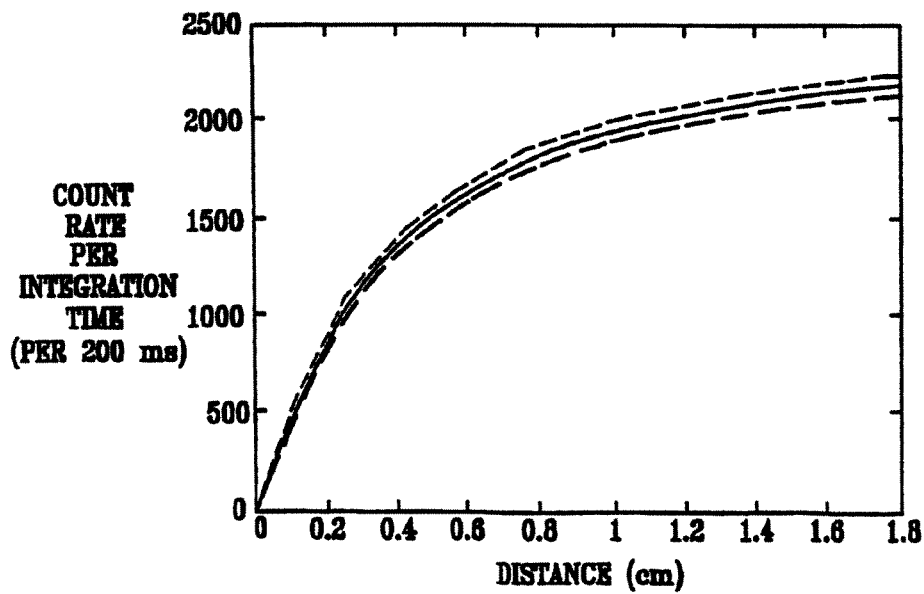

FIGS. 13A-13D are graphs showing experimental results measured in accordance with an embodiment of the present invention. FIGS. 13A, 13B, and 13C are graphs showing energy spectrums using 2% BaSO4 high Z agent depths of 1 cm, 2 cm, and 3 cm, respectively, in accordance with an embodiment of the present invention. Each graph shows a BaSO4 XRF spectral line 180 and a Compton backscattering spectral line 182, measured at a backscattering angle of 180 degrees. As can be seen in the graphs, the XRF photon count rate depends on the depth of high Z agent (BaSO4). FIG. 13D is a plot of the integral under the BaSO4 XRF spectral line vs. high Z agent depth, which also illustrates this dependency of photon count rate on depth of high Z agent, in accordance with an embodiment of the present invention. (The solid line shows the mean count rates, and the dashed lines show plus or minus one standard deviation.)

Analysis of the XRF data that are received from the capsule is generally similar to the analysis performed in embodiments described hereinabove. However, XRF photon counts decrease in the presence of a polyp or other anatomical anomaly, while Compton scattering photon counts increase in the presence of a polyp or other anatomical anomaly.

In accordance with an embodiment of the present invention, both Compton scattered photons and XRF photons counts are measured, and the combined information is utilized to identify the presence of a polyp or other anatomical anomaly. In this XRF/Compton embodiment, the two different types of radiation are separately counted, by evaluating different energy windows corresponding to the two separate energies. Typically, the photon energy of the radiation source is selected such that incident photons from the capsule have a sufficiently high energy so that the approximately 180-degree Compton scattered energy is well separated from the XRF of the contrast agent. Use of both XRF and Compton scattered photon counts typically improves the statistics derived from the received photons.

In an embodiment of the present invention, the combination of Compton scattering photons and XRF photons is used to estimate the absolute distance from each of the detectors on the capsule to the colon inner lumen wall. This information is then used (typically retrospectively, when analyzing the data from the capsule) to reconstruct the inner colon wall surface curvatures as a function of time (or as a function of another parameter, such as distance traveled in the colon, typically as determined using information from the MEMS sensors or information based on the autocorrelation function of the count rates from the various detectors).

In some embodiments, the following absorption equation is used to estimate the distance from the colon wall to the capsule at any given time:

$$I = \sigma(C,D) I_0 * \exp(-\mu x)$$

where:
I is the photon intensity (for a specific energy window) measured by the detector;
$\sigma(C,D)$ is a function describing the measurement efficiency that depends on collimation geometry and detector efficiency;
$I_0$ is the photon intensity at the radiation source (for the same specific energy window);
$\mu$ is the absorption coefficient of the colon contents, which depends on the overall chemical composition and specific density; and
x is the distance in centimeters.

For some application, a method is provided for estimating the absorption coefficient $\mu$. The following observations will aid in understanding the description of this method hereinbelow:

The probability of Compton scattering interaction depends on electron density, and is therefore linearly proportional to the density of the colon contents;

Most photon absorption in the contrast agent (both on the way from the capsule and on the way back to the capsule after Compton scattering) is due to photoelectric interaction, which varies as a function of Z; and The density of the material within the colon is similar to the density of the material outside the colon and generally in the body (as far as Compton scattering interaction probabilities are concerned).

The method for estimating the absorption coefficient $\mu$ of the colon contents (including the contrast agent) typically includes determining which detectors on the capsule were in contact with the wall of the small intestine at any given time. This determination is typically made by identifying which detectors at any given time were recording a very low level of XRF, as this is an indication that the detectors were in contact with the wall. (XRF is measured at a substantial level in response to the incoming photons passing through the contrast agent. However, photons striking a detector that is in contact with the small intestine wall pass through essentially no contrast agent.) This determination is typically made by analyzing the data recorded in external recording unit 52. An evaluation is made of the mean Compton scattering photon count recorded for each detector when it was in contact with the small intestine wall. This corresponds to x=0 in the absorption equation shown above; separating the capsule's detectors from the wall of the colon by at least a known minimum separation distance. The detector which is recording the smallest distance is, therefore, at the known minimum separation distance. In some embodiments, this separation is achieved using extenders, such as described with reference to FIG. 10A or 10B. This separation is performed when the capsule enters the colon. Entry of the capsule into the colon can be detected using a variety of methods, such as those described hereinabove; and calculating the absorption factor $\mu$ of the colon contents including the contrast agent, using Equation 11 and the Compton scattered count rates measured in the first two steps of this method.

Using this calculated value of $\mu$, the time-varying distance from any detector to a near portion of the colon wall is calculated, for that detector's entire period of movement through the colon. In an embodiment, this calculation is based on a model using a semi-log graph, where the count rate is on the y-axis and the distance is on the x-axis. The slope of such a graph is the calculated $\mu$, based on the measurements made in the first two steps of the $\mu$ calculation method.

In an embodiment of the present invention, detecting that the capsule has reached the area of clinical interest comprises detecting X-ray fluorescence (XRF) photons that are substantially different for the stomach, small intestine, and colon. As the capsule travels in the GI tract, the XRF count rate is measured and evaluated per time period. In the stomach, the XRF count rate is expected to be at a moderate level, as a portion of the oral contrast agent administered several hours earlier may still remain. As the capsule enters the small intestine, the XRF count is reduced significantly, because the capsule comes in contact with or nearly comes in contact with the small intestine wall, so there is insufficient space for a substantial amount of fluorescing contrast agent between the detector and the wall. Subsequently, as the capsule enters the colon, XRF counts increase, since the colon is filled with the contrast agent well-mixed along its length. (It is noted that some segments of small intestine are in close proximity of portions of the colon, such that when the capsule is in one of these segments, the XRF count may increase for some of the detectors because of contrast agent in the adjacent portion of the colon (and not because of local contrast agent in the small intestine). This increased XRF count persists until the capsule continues its travel and enters a portion of the small intestine that is not in such close proximity of the colon.)

Alternatively, detecting that the capsule has reached the area of clinical interest comprises using a pH sensor and/or a pH-sensitive coating for the capsule. For applications in which the area of clinical interest includes the colon, the pH sensor is typically configured to detect a reduction of acidity, and the pH-sensitive coating is configured to dissolve in the characteristic pH of the colon.

Alternatively, for detecting that the capsule has reached the colon, the capsule comprises a trigger that is set to switch the capsule on once it passes near an externally-fixed sticker placed on the lower abdomen near the proximity of the entrance to the colon. Such a trigger may comprise, for example, an active oscillating circuit on the sticker. As the capsule comes close to the sticker, a passive resonant circuit in the capsule draws energy from the oscillating on the sticker, and this triggers the capsule to start operating. Similar devices are commonly used in anti-theft systems in stores and libraries.

Alternatively, for detecting that the capsule has reached the colon, the capsule comprises a pressure sensor that is adapted to measure pressure changes within the GI tract. As the capsule passes through the GI tract, pressure measurements are continuously monitored. In the stomach, pressure changes are generally infrequent, e.g., every few minutes. When pressure changes become more frequent and rhythmic, this may indicate that the capsule has entered into the small intestine, where it is expected to travel for 2-5 hours on average. Once the rhythmic pressure changes cease and less regular pressure waves and less frequent pressure waves are monitored, it is likely that the capsule has entered the large intestine where it is expected to remain for between 24 and 72 hours on average.

These techniques for detecting that the capsule has reached the area of interest may be utilized separately or in combination. When used in combination, information is typically correlated from a number of independent sensors as described above, and analyzed in order to ascertain that the capsule has reached the area of interest, e.g., the colon. (Alternatively, the capsule is in substantially continuous operation in the GI tract.)

Typically, after the capsule is expelled, the data are post-processed and presented to an expert viewer. In some embodiments, the data are presented as a series of cross sectional reconstructions to the viewer. An expert viewer is able to identify the irregular features that are not usually found in the inner colon lumen during a contraction of the colon muscles. Specifically, the system enables the detection of "bumpy" and irregular bulging features in the colon wall, which may be polyps or other suspect anatomical deformations.

In an embodiment of the present invention, the data from the capsule may be presented to the physician in a graphical format (see FIGS. 14A-C and 15A-C) that does not give actual imaging information, but rather displays the information in a processed graphical representation that helps the physician to determine if there is a likelihood of a polyp or other anatomical anomaly that may harbor cancer and require colonoscopy.

For applications in which radiation source 60 emits photons having two or more different energies, the basic analyzed data unit may be a relationship (e.g., a ratio or difference) between the high-energy counts and the low energy counts. Alternatively or additionally, the basic analyzed data unit is the count for each of the energy windows.

In an embodiment of the present invention, the ratio between the high energy count rate and the low energy count rate backscattered from the colon contents and beyond is used to calibrate the actual distance of the capsule from the colon wall. This is possible because the ratio of the photon flux at the different energies is related to, e.g., proportional to, the actual distance. This property is especially useful since the concentration of the contrast agent may change as the capsule travels from the right colon, where the colon contents are fluid, to the left colon and the rectum, where the colon contents are usually less fluid, or even semi-rigid. Therefore, the average flux of photons per centimeter depth of contrast agent decreases as the concentration of the contrast agent increases. (Water flows out of the colon; hence the contrast agent concentration in the colon increases, because the agent does not leave the colon.)

In an embodiment of the present invention, a capsule such as capsule 50 is adapted to detect Compton backscattered photons, typically those photons emerging from a backscattering process of 180° (+/−20° to 30°) relative to the incident photons, depending on the detector energy resolution and the detector collimation (if collimated). For multiple energy window applications, the count rates for different energy windows are used as the basic data for the imaging process. In particular, for each detector, the electronics associated with its dedicated channel sum the number of photons that hit the detector at each of the predefined energy windows according to Compton backscattered energy principles. (Other energy windows are set to detect XRF photons coming from the contrast agent that is being illuminated.)

FIGS. 14A-C and 15A-C schematically illustrate surfaces representing morphologies of the GI tract, generated in accordance with an embodiment of the present invention. A dynamic tracking algorithm is provided for detecting polyps in the GI tract, such as in the colon, and discriminating them from other morphologies normally found in the colon, such as curving colon walls, haustra rings, and folds of the colon. This algorithm makes use of movement of the capsule within the colon to detect and separate the morphology of polyps from the morphologies of the other normal structures in the colon.

In this embodiment, the emitted radiation is typically configured so as to "illuminate" all or a portion of the volume surrounding the capsule. Alternatively, the collimation on the emitted radiation is configured to selectively illuminate certain sectors of the volume surrounding the capsule while leaving other sectors unilluminated. This latter configuration may serve to better detect anatomical formations within the colon as the capsule moves, detecting the objects of interest as they move from "shadow" to "light."

In the following description of the dynamic tracking algorithm, for the sake of simplicity, it is assumed that the radiation detectors are spread over a 2D rectangular surface. It is also assumed that the data from the detectors are mapped onto a 2D rectangular surface where each detectors data are represented by a measured reading of a property such as the count rate per integration time in a certain energy window corresponding to the Compton backscattered photon energy window. In this manner, the 3D internal colon lumen is mapped onto the 2D rectangular surface.

At a first step of the dynamic tracking algorithm, for every subdivision on the 2D representing surface, a relative distance that each collimator "sees" is calculated, e.g., using the matrix algorithm of Equation 1, described hereinabove. Surfaces 120A, 120B, and 120C of FIGS. 14A, 14B, and 14C, respectively, and surfaces 122A, 122B, and 122C of FIGS. 15A, 15B, and 15C, respectively, are exemplary representations of such a relative distance-indicating surface, at respective points in time.

At a second step of the algorithm, a difference is calculated between the reading representing the subdivision and the respective readings representing all of the neighboring subdivisions (up to 6 neighbors on the 2D surface).

At a third step, a threshold is calculated, e.g., +/−σ relative to the subdivision value, based on a Poisson distribution. For example, if Nij is the reading at a subdivision ij (after the analysis described in the first step), the threshold will be one sigma (i.e., +/− the square root of Nij). Only readings at least one sigma from the subdivision value are used at the fourth step, described immediately below.

Figure 14A:
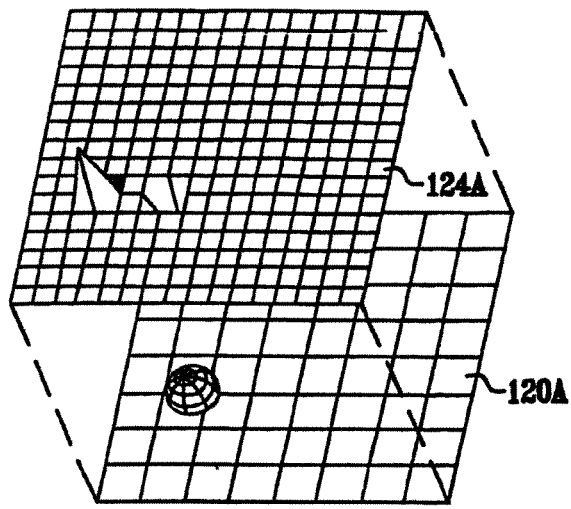
FIGS. 14A-C and 15A-C are schematic illustrations of surfaces representing morphologies of the GI tract, generated in accordance with an embodiment of the present invention
Figure 14B:
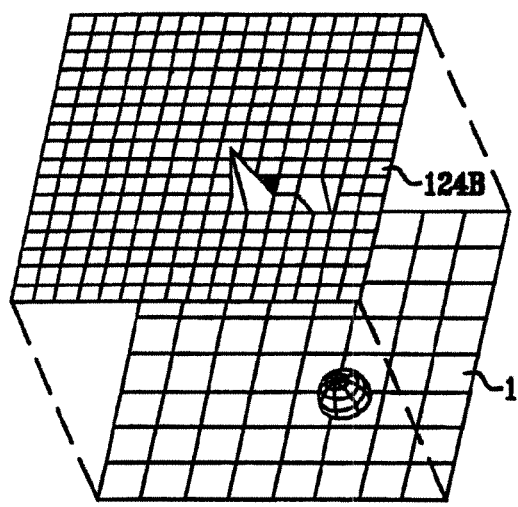
Figure 14C:
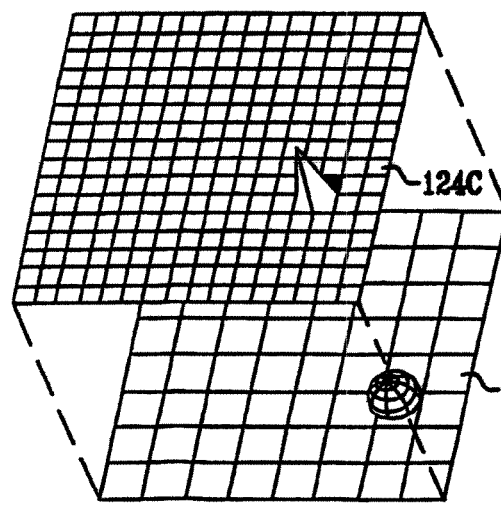
Figure 15A:
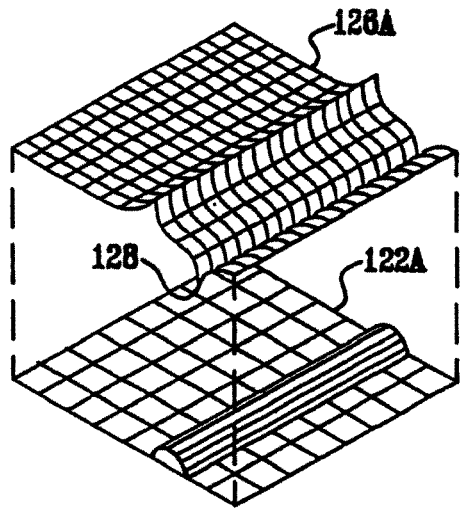
Figure 15B:
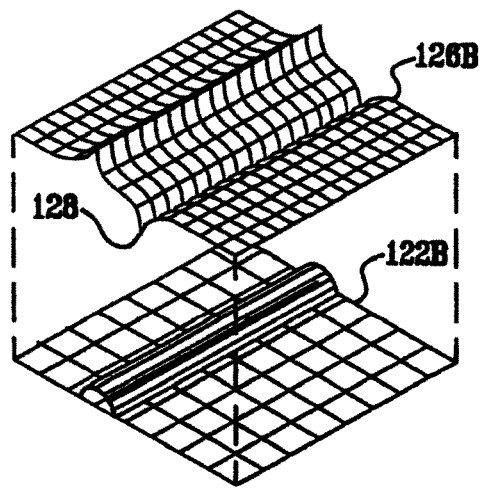
Figure 15C:
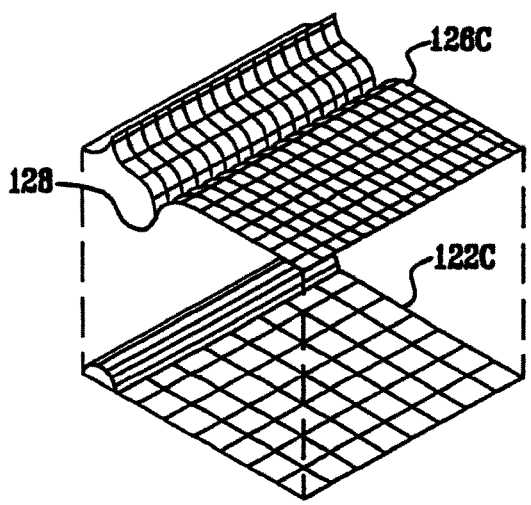

At a fourth step, a new 2D surface is plotted, in which the pixels represent differences between the subdivisions of the first 2D map (i.e., of surfaces 120A-C and 122A-C of FIGS. 14A-C and 15A-C, respectively). The outcome of this representation is a series of 2D morphologies in time that represent time derivatives outlining the movement of the capsule within the colon and showing different morphologies as the capsule travels. Surfaces 124A, 124B, and 124C of FIGS. 14A, 14B, and 14C, respectively, and surfaces 126A, 126B, and 126C of FIGS. 15A, 15B, and 15C, respectively, are exemplary representations of surfaces representing such differences, at respective points in time. For example: The morphology of a moving front (made up of a few correlated routes) is a line, such as a line 128 of FIGS. 15A-C. The morphology of a moving front that has cylindrical symmetry (in the 3D capsule space) appears as a linear ridge across the 2D difference space, such as ridge 130 of FIGS. 15A-C. Such a moving front may be related to wall motion or capsule motion in relation to the walls. A moving object that has isolated morphology may be related to polyps or other anatomical anomalies, as shown in FIGS. 14A-C.

At a fifth step of the algorithm, these 2D difference maps are shown as an animated series to the expert viewer in order to assist him to evaluate possible anomalies, such as polyps.

In some embodiments, the algorithm uses an autocorrelation function based on readings from detectors to estimate local 3D movements of the capsule. Use of such an autocorrelation function generally improves signal to noise. This information can then be used to correlate readings from adjacent subdivisions and hence to increase the integration times by estimating the readings based on a number of integration time periods rather than using single integration times. This increase in integration time by averaging correlated readings generally reduces noise.

The dynamic resolution provided by this algorithm generally allows the resolution of polyps at relatively large distances from the capsule, even using a relatively small number of detectors. This is the case even though the relatively small number of detectors are not collimated or are slightly collimated (and hence they overlap in their field of view), which, without the use of such an algorithm, would generally result in a relatively low static resolution (which is determined by radiation source collimation).

Other algorithms which make use of dynamic analysis may be used to detect polyps or other anatomical anomalies in the colon and discriminate between them and normal colon wall movements (e.g., colon muscle contractions) and capsule movements within the colon. In particular, algorithms that use dynamic analyses analogous to those described may be adapted for use with the embodiments described above, to enhance robustness and improve noise immunity to spatial and temporal variations. In particular, dynamic analysis may be used in conjunction with the static analysis to improve the detection and evaluation of abnormalities such as polyps.

In an embodiment of the present invention, a processing unit is incorporated within the capsule so that limited data analysis can be done within the capsule in real time. In particular, the capsule may calculate the autocorrelation function of the measured data and combine this information in order to determine if the capsule is moving within the colon due to gravitational or other external forces other than pressure-induced mass movements. In particular, the combination of the MEMS accelerometer and the autocorrelation function can help determine if the capsule is stationary or moving within the colon. The capsule accordingly continues to operate the movement of the radiation source until the capsule comes to rest.

In an embodiment of the present invention, shield 68 may comprise, at least in part, a magnetic material, such that the shield functions as part of actuator 84 (for example, when the actuator comprises a voice coil actuator). In this embodiment, a dedicated magnet is generally not needed.

In an embodiment of the present invention, methods are provided for detecting and discriminating between gas in the colon and anatomical abnormalities, such as polyps. From time to time, gas bubbles form within the colorectal lumen. These bubbles may be mistakenly identified as possible polyps or another anatomical deformation in the colon. In this embodiment, a set of algorithmic tools and supporting hardware is implemented to help distinguish between air bubbles and polyps or other anatomical deformations within the colon. These algorithmic tools include, but are not limited to: Compton scattering from gas is substantially lower (typically almost non-existent) than that from tissue (both normal and abnormal). Thus, a gas bubble appears as reduced Compton scattering in all the energy windows. Further, the relationship (e.g., ratio or difference) between high and low energies may not change much in the presence of a gas bubble. Therefore, recognition of reduced Compton scattering in all energy windows and smaller changes in the above relationship is an indication of the presence of gas, because the photons pass through less contrast agent. In addition to Compton scattered photons, the capsule also is typically adapted to detect X-Ray fluorescence photons emitted by the high Z atoms of the contrast agent. Air and other gases in the colon do not emit XRF, due to the lower Z number and predominately due to lower density. This enables differentiation between gas pockets and polyps based on the ratio between Compton scattered photons and X-ray fluorescence photons. Upon formation, gas bubbles tend to rise to the uppermost part of the lumen, because of gravity. Therefore, using tilt relative to center of gravity information from the MEMS chip, a determination is made whether a possible bubble has been detected. Using the information on the direction of gravity, it is possible to ascertain where the gas bubble is with respect to any solid angle sectors that may be detecting changes in count rates associated with the gas bubble. Gas bubbles, when stable, have a flat surface at their bottom. Therefore, they register differently than a polyp or other bulging anatomical abnormalities within the colon. Gas bubbles, when unstable, travel away from gravitational pull. Therefore, using information from the MEMS chip, a determination is made whether a possible bubble is traveling near the capsule. In the final part of the colon and in the rectum, gas may form and later be released from the anus. This registers as a gradual decrease in XRF radiation counts and Compton scattering counts over seconds and minutes, followed by a sharp return to a higher value once the gas has been released. In order to reduce the amount of gas in the colorectal lumen, a gas absorbing material such as a charcoal compound, or a compound found in commercial products intended for absorption of gas in the GI tract, may be mixed with or administered together with the contrast agent. In some embodiments, the presence of a gas bubble is detected using sound waves (e.g., ultrasound). Gas bubbles have a distinctly different acoustic reflective property compared to that of polyps and other anatomical anomalies within the colon lumen.

In an embodiment of the present invention, an energy-saving protocol is used to save battery power when the capsule is traveling in the GI tract before entering the colon. In accordance with such a protocol, one or more of the techniques described hereinabove for detecting that the capsule has reached the colon are used. Once arrival in the colon has been detected, the capsule starts data collection in order to detect polyps within the colon. This data collection typically lasts on average between 24 and 72 hours. In order to minimize radiation exposure from the capsule, the capsule is designed to emit radiation only when it may be about to move. Such imminent motion may be detected, for example, by sensing the changes in pressure of the colon contents; the capsule is activated when a pressure time-dependant gradient passes a certain threshold. Alternatively or additionally, the capsule may be activated if the capsule changes its tilt angle relative to the earth's gravitational pull vector (this may be detected with the MEMS accelerometer chip). A change in this relative tilt above a certain threshold may indicate that the capsule is about to move. Alternatively or additionally, the capsule may use a combination of these criteria for determining when to activate the radiation source.

Alternatively or additionally, the trigger for activating the detectors may comprise a pressure gauge activating the capsule to switch on the detector channels and other electronic circuits that have been disabled to save energy. After pressure is reduced, the capsule reverts to a quiescent mode of operation, optionally after a delay.

In an embodiment of the present invention, radiation detectors placed on the subject's body are used to track the position of the capsule. Measuring the relative intensity of the detected radiation from a few detectors with known relative positions between them enables tracking of the position of the capsule in real time. The position of the detectors may be tracked by a magnetic location system or another position tracking system known in the art.

In an embodiment of the present invention, the subject is administered an oral agent that has a high Z (i.e., an atomic number of at least 50, typically between 60 and 100) and emits relatively high X-ray fluorescence in response to incident gamma and/or X-ray radiation. Such an agent may comprise, for example, barium sulfate iodine-based compounds or Gadolinium-based compounds, which are routinely used as GI tract contrast agents, or other compounds that emit X-ray fluorescence at relatively high energy (32 keV for barium). This material is generally confined to the GI lumen. The high Z agent fills the volume of the inner colorectal lumen and aids in the detection of polyps and other anatomical deformations by indicating where there are volumes not occupied by the high Z agent.

Except as described hereinbelow, the principles of operation of this embodiment are generally similar to that of embodiments described hereinabove. As in these other embodiments, the capsule emits gamma and/or X-ray radiation to illuminate the vicinity of the capsule. However, unlike in these other embodiments, the purpose of this illumination is to excite the high Z agent to emit X-ray fluorescence (XRF). The X-ray radiation emitted by the XRF process is then detected and processed by the capsule.

In an embodiment of the present invention, capsule 50 is tracked by a navigation system that adds position information to the capsule data. Such a navigation system may comprise, for example, a set of radio receivers that track the capsule by measuring, at different positions on the subject's body, the relative amplitudes of RF signals transmitted by the capsule. Other embodiments utilize ultrasound-based localization, wherein the capsule serves as a transponder to signals coming from a few locations on the subject's body, and time-of-flight measurements provide position location. Other position-location technologies known in the art, such as magnetic-field based location sensing, are used for some applications.

In an embodiment of the present invention, capsule 50 comprises electrically-conductive electrodes coupled to its surface, and a pulse generator in the capsule that is controlled by the capsule's microcontroller. In this embodiment, the capsule is adapted to stimulate the colon electrically, thereby inducing a controlled mass movement. The capsule typically repeatedly performs the following steps: (a) awakens from a quiescent mode and begins to acquire data, (b) stimulates the colon to effect mass movement, and (c) upon the cessation of mass movement, ceases to acquire data and reenters the quiescent mode. In this manner, the capsule can be controlled and data acquired at relevant times. The subject may also be informed that the capsule has started its imaging within the colon. Alternatively, the subject may choose when to start such process. In such a case, the entire screening of the colon may have a short duration. In this case, the stool may be soft and the subject may elect to use a toilet during the few minutes required to complete the screening of the colon and rectum.

In an embodiment of the present invention, colon muscles are observed during a contraction, using the observation and analysis techniques described herein. Healthy colon muscles contract in a generally cylindrically symmetrical fashion. The potential presence of an anatomical anomaly is detected by observing a deviation from such cylindrical symmetry. Such an anomaly may be a polyp or other anatomical anomaly that may harbor cancerous or pre-cancerous tumors. Deviations along the path of the colon from one area to another may also indicate the presence of an anatomical abnormality.

In an embodiment of the present invention, the capsule's power source comprises a "nuclear battery," utilizing the radioactive material in the capsule as a beta emitter.

It is noted that whereas some embodiments of the present invention are described herein with respect to causing the subject to swallow a contrast agent such as barium (which increases absorption of photons, and thus provides a way to differentiate between the wall of the GI tract and the contents of the lumen), in other embodiments of the present invention the subject instead swallows a contrast agent which has reduced absorption relative to the wall of the GI tract. For example, nutritional fibers have lower absorption than the absorption of the GI tract wall and tissue outside of the GI tract, and, therefore, when the capsule passes by a polyp or other abnormality, the recorded Compton scattered photons will decrease. As used herein, including in the claims, "contrast agent" includes both positive-attenuation and negative-attenuation contrast agents.

Although in some embodiments of the present invention capsule 50 and/or data-recording unit 52 are described as performing certain calculations and/or analyses, all or a portion of these calculations and/or analyses may be performed instead by external data analysis software and/or hardware. Similarly, in some embodiments, calculations and/or analyses described herein as being performed by external data analysis software and/or hardware may be performed by capsule 50 and/or data-recording unit 52.

Although some embodiments of the present invention are described with respect to inspecting the colon of a subject, some of the techniques described herein may also be applicable to other portions of the GI tract, and/or to other body lumens, such as blood vessels, mutatis mutandis.

For simplicity, some embodiments of the present invention are described herein with respect to a scattering angle of 180°, but typically include a range around 180° as well. For example, the range may be 180°+/− a range parameter, where the range parameter is typically less than 10°, 20°, or 30°.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

What is claimed is:

1. An apparatus for detecting a polyp or cancer in a gastrointestinal (GI) tract of a subject, comprising:
    a capsule with a capsule housing, said capsule adapted to be swallowed by a subject, said capsule comprising:
    at least one radiation source emitting X-ray or gamma radiation and having at least one collimator configured to collimate radiation emitted by the at least one radiation source; and
    at least one radiation detector configured to detect in a first energy window X-ray fluorescence radiation from a contrast agent composition consisting essentially of a stable and non-radioactive isotope and being excited by the emitted and collimated X-ray or gamma radiation, and to detect in a second energy window or additional energy windows, Compton-backscattered radiation from the contrast agent and the wall of the GI tract produced in response to the emitted and collimated X-ray or gamma radiation;
    an accelerometer that is used to determine if the capsule is stationary or moving and determine a tilt angle of the capsule relative to the earth center of gravity;
    the apparatus further comprising a control unit configured to distinguish between a gas bubble in the GI tract and a polyp or cancer at the specific location based on identifying one or more of the following:
    a. a reduction in the count rate of Compton backscattered radiation at the location in all energy windows;
    b. a reduction in the count rate of Compton backscattered radiation at the location in all energy windows and smaller changes in the difference between the count at high and low energies;
    c. a reduction in the count rate of X-ray fluorescence radiation at the location;
    d. the tilt angle of the capsule relative to center of gravity information to ascertain a relative location of the gas bubble or polyp or cancer; and
    e. the surface of the detected gas bubble or polyp or cancer to determine if it is a gas bubble with a flat bottom surface or a polyp or cancer with bulging anatomical abnormalities.

2. The apparatus according to claim 1, wherein the control unit is integrated in or attached to the capsule.

3. The apparatus according to claim 1, wherein the at least one radiation source comprises a radioisotope.

4. The apparatus according to claim 1, wherein the control unit is configured to estimate a distance from a site of the capsule to a wall of the GI tract.

5. The apparatus according to claim 1, wherein the distance is estimated from an intensity measurement of the Compton backscattered radiation.

6. The apparatus according to claim 4, wherein the distance is estimated from an intensity measurement of the X-ray fluorescence (XRF) radiation generated responsive to the emitted radiation.

7. The apparatus according to claim 1, wherein the radiation source emits the radiation from the capsule only during a portion of a time that the capsule is in the GI tract.

8. The apparatus according to claim 7, wherein the capsule comprises an actuator adapted to move at least one of the radiation source and the shield, such that the radiation shield does not block the radiation emitted from the radiation source during the portion of the time.

9. The apparatus according claim 1, wherein the capsule comprises at least one radiation shield.

10. The apparatus according to claim 9, wherein the at least one radiation shield is configured to prevent radiation from being emitted from the radiation source in directions other than a single confined solid sector relative to a sphere surrounding the capsule.

11. The apparatus according to claim 1, wherein the control unit is adapted to detect that the capsule has reached an area of clinical interest within the GI tract.

12. The apparatus according to claim 11, wherein the control unit includes means for activating the radiation detector and electronic circuitry upon relative movement between the capsule and the colon wall.

13. The apparatus according to claim 1, wherein the at least one radiation detector detects in response to the emitted radiation a first signal and a second signal inside a GI tract of the subject, and wherein the control unit processes the first signal to generate a first image of the GI tract of a region where the first signal was detected, and wherein the control unit processes the second signal to generate a second image of the GI tract of a region where the second signal was detected; and detects movement of the capsule relative to the GI tract by comparing the first and second generated images.

14. An apparatus for detecting a polyp or cancer in a gastrointestinal (GI) tract of a subject, comprising:
    a capsule with a capsule housing, said capsule adapted to be swallowed by a subject, said capsule comprising:
    at least one radiation source emitting X-ray or gamma radiation;
    at least one radiation detector configured to detect in a first energy window X-ray fluorescence radiation from a contrast agent composition excited by the emitted X-ray or gamma radiation, and to detect in a second energy window or additional energy windows, Compton-backscattered radiation from the contrast agent and the wall of the GI tract produced in response to the emitted X-ray or gamma radiation,
    an accelerometer that is used to determine if the capsule is stationary or moving and determine a tilt angle of the capsule relative to the earth center of gravity;
    the apparatus further comprising a control unit configured to:
    estimate a distance between the capsule and the wall of the GI tract from the Compton-backscattered radiation and the X-ray fluorescence radiation information; and
    distinguish between a gas bubble in the GI tract and a polyp or cancer at the specific location based on identifying one or more of the following:
    a. a reduction in the count rate of Compton backscattered radiation at the location in all energy windows;

b. a reduction in the count rate of Compton backscattered radiation at the location in all energy windows and smaller changes in the difference between the count at high and low energies;
c. a reduction in the count rate of X-ray fluorescence radiation at the location;
d. the tilt angle of the capsule relative to center of gravity information to ascertain a relative location of the gas bubble or polyp or cancer; and
e. the surface of the detected gas bubble or polyp or cancer to determine if it is a gas bubble with a flat bottom surface or a polyp or cancer with bulging anatomical abnormalities.

15. The apparatus of claim 14, further comprising at least two electrodes spaced on the capsule, with at least one electrode emitting electromagnetic pulses and at least one other electrode detecting a response signal responsive to the emitted electromagnetic pulses; and wherein the electromagnetic pulses comprise RF pulses and the electrodes comprise antennae.

16. The apparatus of claim 14, further comprising at least two electrodes spaced on the capsule, with at least one electrode emitting electromagnetic pulses and at least one other electrode detecting a response signal responsive to the emitted electromagnetic pulses; and wherein the electromagnetic pulses comprise low-voltage pulses and the electrodes comprise galvanic electrodes.

17. The apparatus of claim 14, wherein the control unit is integrated in or attached to the capsule.

18. The apparatus of claim 13, wherein the control unit computes an average of the processed first and second signals while the capsule is moving through the GI tract, and compares a new first signal with a magnitude of the computed average, and lengthens or shortens a time interval between acquisition of subsequent first and second signals depending if the magnitude of the computed average and the new first signal is smaller or greater than a predetermined threshold value.

19. An apparatus for detecting a polyp or cancer in a gastrointestinal (GI) tract of a subject, comprising:
a capsule with a capsule housing, said capsule adapted to be swallowed by a subject, said capsule comprising:
at least one radiation source emitting X-ray or gamma radiation;
at least one radiation detector configured to detect in a first energy window X-ray fluorescence radiation from a contrast agent composition excited by the emitted X-ray or gamma radiation, and to detect in a second energy window or additional energy windows, Compton-backscattered radiation from the contrast agent and the wall of the GI tract produced in response to the emitted X-ray or gamma radiation,
an accelerometer that is used to determine if the capsule is stationary or moving and determine a tilt angle of the capsule relative to the earth center of gravity;
the apparatus further comprising a control unit configured to distinguish between a gas bubble in the GI tract and a polyp or cancer at the specific location based on identifying one or more of the following:
a. a reduction in the count rate of Compton backscattered radiation at the location in all energy windows;
b. a reduction in the count rate of Compton backscattered radiation at the location in all energy windows and smaller changes in the difference between the count at high and low energies;
c. a reduction in the count rate of X-ray fluorescence radiation at the location;
d. the tilt angle of the capsule relative to center of gravity information to ascertain a relative location of the gas bubble or polyp or cancer; and
e. the surface of the detected gas bubble or polyp or cancer to determine if it is a gas bubble with a flat bottom surface or a polyp or cancer with bulging anatomical abnormalities.

20. The apparatus according to claim 1, wherein the at least one collimator is configured to rotate with respect to the housing.

21. The apparatus according to claim 14, wherein the control unit is configured to estimate the distance between the capsule and the wall of the GI tract based on an inverse relationship between the distance and photon flux of the detected Compton-backscattered radiation and a relationship between the detected X-ray fluorescence radiation and the distance between the capsule and the wall of the GI tract.

* * * * *